United States Patent
Lu et al.

(10) Patent No.: US 9,289,448 B2
(45) Date of Patent: Mar. 22, 2016

(54) COMPOSITIONS AND METHODS FOR TREATING ALZHEIMER'S DISEASE AND OTHER TAUOPATHIES

(71) Applicant: Board of Trustees Of The Leland Stanford Junior University, Palo Alto, CA (US)

(72) Inventors: Bingwei Lu, Stanford, CA (US); Seongsoo Lee, Stanford, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/216,065

(22) Filed: Mar. 17, 2014

(65) Prior Publication Data

US 2015/0174150 A1 Jun. 25, 2015

Related U.S. Application Data

(60) Provisional application No. 61/792,009, filed on Mar. 15, 2013.

(51) Int. Cl.
*A61K 31/713* (2006.01)
*A61K 31/44* (2006.01)
*A61K 48/00* (2006.01)

(52) U.S. Cl.
CPC .............. *A61K 31/713* (2013.01); *A61K 31/44* (2013.01); *A61K 48/00* (2013.01)

(58) Field of Classification Search
CPC ...... A61K 31/713; A61K 31/44; A61K 48/00
USPC ........................................................ 514/357
See application file for complete search history.

(56) References Cited

PUBLICATIONS

Kapuria et al. Cancer Research, 2010, 70(22) 9265-9276.*
Seshadri, S. et al. Genome-wide analysis of genetic loci associated with Alzheimer disease. JAMA 303, 1832-1840 (2010).
Kim, E. & Sheng, M. PDZ domain proteins of synapses. Nat Rev Neurosci 5, 771-781 (2004).
Yu, W. et al. A critical role for the PAR-1/MARK-tau axis in mediating the toxic effects of Abeta on synapses and dendritic spines. Hum Mol Genet 21, 1384-1390 (2011).
Lee, F. K. et al. The role of ubiquitin linkages on alpha-synuclein induced-toxicity in a *Drosophila* model of Parkinson's disease. J Neurochem 110, 208-219 (2009).
Grima, B. et al. The F-box protein slimb controls the levels of clock proteins period and timeless. Nature 420, 178-182 (2002).
Martin, S. G. & St Johnston, D. A role for *Drosophila* LKB1 in anterior-posterior axis formation and epithelial polarity. Nature 421, 379-384 (2003).
Ko, H. W., Jiang, J. & Edery, I. Role for Slimb in the degradation of *Drosophila* Period protein phosphorylated by Doubletime. Nature 420, 673-678 (2002).
Bartholomeusz GA et al. Blood. 109:3470-8, (2007) Activation of a novel Bcr/Abl destruction pathway by WP1130 induces apoptosis of chronic myelogenous leukemia cells.
Kapuria V et al. Cancer Res. 70:9265-76, (2010) Deubiquitinase Inhibition by Small-Molecule WP1130 Triggers Aggresome Formation and Tumor Cell Apoptosis.
Spires et al. (2005) J. Neurosci. 25:7278-7287.
Reddy et al. (2008) Trend. Mol. Med. 14:45-53.
Selkoe (2008) Brain Res. 192:106-113.
Hardy et al. (2002) Science 297:353-356.
Hammond et al., Nature Rev Gen 2: 110-119 (2001).
Sharp, Genes Dev 15: 485-490 (2001).
Davidson and McCray, Nat Rev Genet. May 2011;12(5):329-40.
Guo, S. & Kemphues, K. J. par-1, a gene required for establishing polarity in C. elegans embryos, encodes a putative Ser/Thr kinase that is asymmetrically distributed. Cell 81, 611-620 (1995).
Matenia, D. & Mandelkow, E. M. The tau of MARK: a polarized view of the cytoskeleton. Trends Biochem Sci 34, 332-342 (2009).
Hurov, J. & Piwnica-Worms, H. The Par-1/MARK family of protein kinases: from polarity to metabolism. Cell Cycle 6, 1966-1969 (2007).
Drewes, G., Ebneth, A., Preuss, U., Mandelkow, E. M. & Mandelkow, E. MARK, a novel family of protein kinases that phosphorylate microtubule-associated proteins and trigger microtubule disruption. Cell 89, 297-308 (1997).
Trinczek, B., Brajenovic, M., Ebneth, A. & Drewes, G. MARK4 is a novel microtubule-associated proteins/microtubule affinity-regulating kinase that binds to the cellular microtubule network and to centrosomes. J Biol Chem 279, 5915-5923 (2004).
Nishimura, I., Yang, Y. & Lu, B. PAR-1 kinase plays an initiator role in a temporally ordered phosphorylation process that confers tau toxicity in *Drosophila*. Cell 116, 671-682 (2004).
Lee, V. M., Goedert, M. & Trojanowski, J. Q. Neurodegenerative tauopathies. Annu Rev Neurosci 24, 1121-1159 (2001).
Timm, T. et al. MARKK, a Ste20-like kinase, activates the polarity-inducing kinase MARK/PAR-1. EMBO J 22, 5090-5101 (2003).
Lizcano, J. M. et al. LKB1 is a master kinase that activates 13 kinases of the AMPK subfamily, including MARK/PAR-1. EMBO J 23, 833-843 (2004).
Wang, J. W., Imai, Y. & Lu, B. Activation of PAR-1 kinase and stimulation of tau phosphorylation by diverse signals require the tumor suppressor protein LKB1. J Neurosci 27, 574-581 (2007).
Hershko, A. & Ciechanover, A. The ubiquitin system. Annu Rev Biochem 67, 425-479 (1998).
Schwartz, A. L. & Ciechanover, A. Targeting proteins for destruction by the ubiquitin system: implications for human pathobiology. Annu Rev Pharmacol Toxicol 49, 73-96 (2009).
Jiang, J. Regulation of Hh/Gli signaling by dual ubiquitin pathways. Cell Cycle 5, 2457-2463 (2006).
Jiang, J. & Struhl, G. Regulation of the Hedgehog and Wingless signalling pathways by the F-box/WD40-repeat protein Slimb. Nature 391, 493-496 (1998).
Winston, J. T. et al. The SCFbeta-TRCP-ubiquitin ligase complex associates specifically with phosphorylated destruction motifs in IkappaBalpha and beta-catenin and stimulates IkappaBalpha ubiquitination in vitro. Genes Dev 13, 270-283 (1999).

(Continued)

*Primary Examiner* — Yevegeny Valenrod

(74) *Attorney, Agent, or Firm* — Davis, Brown, Koehn, Shors & Roberts, P.C.; Sean D. Solberg

(57) ABSTRACT

Compounds, pharmaceutical compositions, and methods of using such compounds and compositions to treat or prevent Alzheimer's disease and related tauopathies through the inhibition of USP-9X and/or enhancement of SCF(β-TrCP).

26 Claims, 29 Drawing Sheets

(56) References Cited

PUBLICATIONS

Ho, M. S., Ou, C., Chan, Y. R., Chien, C. T. & Pi, H. The utility F-box for protein destruction. Cell Mol Life Sci 65, 1977-2000 (2008).

Nijman, S. M. et al. A genomic and functional inventory of deubiquitinating enzymes. Cell 123, 773-786 (2005).

DiAntonio, A. et al. Ubiquitination-dependent mechanisms regulate synaptic growth and function. Nature 412, 449-452 (2001).

Holtzman, D. M., Morris, J. C. & Goate, A. M. Alzheimer's disease: the challenge of the second century. Sci Transl Med 3, 77sr71 (2011).

Xue, L. et al. Tumor suppressor CYLD regulates JNK-induced cell death in Drosophila. Dev Cell 13, 446-454 (2007).

Zhang, Y. et al. PAR-1 kinase phosphorylates Dlg and regulates its postsynaptic targeting at the Drosophila neuromuscular junction. Neuron 53, 201-215 (2007).

Brajenovic, M., Joberty, G., Kuster, B., Bouwmeester, T. & Drewes, G. Comprehensive proteomic analysis of human Par protein complexes reveals an interconnected protein network. J Biol Chem 279, 12804-12811 (2004).

Al-Hakim, A. K. et al. Control of AMPK-related kinases by USP9X and atypical Lys(29)/Lys(33)-linked polyubiquitin chains. Biochem J 411, 249-260 (2008).

Chen, X., Zhang, B. & Fischer, J. A. A specific protein substrate for a deubiquitinating enzyme: Liquid facets is the substrate of Fat facets. Genes Dev 16, 289-294 (2002).

Mortimer, N. T. & Moberg, K. H. The Drosophila F-box protein Archipelago controls levels of the Trachealess transcription factor in the embryonic tracheal system. Dev Biol 312, 560-571 (2007).

Iijima, K., Gatt, A. & Iijima-Ando, K. Tau Ser262 phosphorylation is critical for Abeta42-induced tau toxicity in a transgenic Drosophila model of Alzheimer's disease. Hum Mol Genet 19, 2947-2957 (2010).

Haass, C. & Selkoe, D. J. Soluble protein oligomers in neurodegeneration: lessons from the Alzheimer's amyloid beta-peptide. Nat Rev Mol Cell Biol 8, 101-112 (2007).

Ittner, L. M. & Gotz, J. Amyloid-beta and tau—a toxic pas de deux in Alzheimer's disease. Nat Rev Neurosci 12, 65-72 (2011).

Ittner, L. M. et al. Dendritic function of tau mediates amyloid-beta toxicity in Alzheimer's disease mouse models. Cell 142, 387-397 (2010).

Hoover, B. R. et al. Tau mislocalization to dendritic spines mediates synaptic dysfunction independently of neurodegeneration. Neuron 68, 1067-1081 (2010).

Heidary, G. & Fortini, M. E. Identification and characterization of the Drosophila tau homolog. Mech Dev 108, 171-178 (2001).

Lee, S., Liu, H. P., Lin, W. Y., Guo, H. & Lu, B. LRRK2 kinase regulates synaptic morphology through distinct substrates at the presynaptic and postsynaptic compartments of the Drosophila neuromuscular junction. J Neurosci 30, 16959-16969 (2010).

DiAntonio, A. & Hicke, L. Ubiquitin-dependent regulation of the synapse. Annu Rev Neurosci 27, 223-246 (2004).

Yi, J. J. & Ehlers, M. D. Emerging roles for ubiquitin and protein degradation in neuronal function. Pharmacol Rev 59, 14-39 (2007).

Selkoe, D. J. Alzheimer's disease is a synaptic failure. Science 298, 789-791 (2002).

Xu, J., Taya, S., Kaibuchi, K. & Arnold, A. P. Spatially and temporally specific expression in mouse hippocampus of Usp9x, a ubiquitin-specific protease involved in synaptic development. J Neurosci Res 80, 47-55 (2005).

Xu, J. Age-related changes in Usp9x protein expression and DNA methylation in mouse brain. Brain Res Mol Brain Res 140, 17-24 (2005).

Chin, J. Y. et al. Microtubule-affinity regulating kinase (MARK) is tightly associated with neurofibrillary tangles in Alzheimer brain: a fluorescence resonance energy transfer study. J Neuropathol Exp Neurol 59, 966-971 (2000).

Augustinack, J. C., Schneider, A., Mandelkow, E. M. & Hyman, B. T. Specific tau phosphorylation sites correlate with severity of neuronal cytopathology in Alzheimer's disease. Acta Neuropathol (Berl) 103, 26-35 (2002).

Perez, M. et al. Characterization of a double (amyloid precursor protein-tau) transgenic: tau phosphorylation and aggregation. Neuroscience 130, 339-347 (2005).

Zempel, H., Thies, E., Mandelkow, E. & Mandelkow, E. M. Abeta oligomers cause localized Ca(2+) elevation, missorting of endogenous Tau into dendrites, Tau phosphorylation, and destruction of microtubules and spines. J Neurosci 30, 11938-11950 (2010).

Gylys, K. H. et al. Synaptic changes in Alzheimer's disease: increased amyloid-beta and gliosis in surviving terminals is accompanied by decreased PSD-95 fluorescence. Am J Pathol 165, 1809-1817 (2004).

Almeida, C. G. et al. Beta-amyloid accumulation in APP mutant neurons reduces PSD-95 and GluR1 in synapses. Neurobiol Dis 20, 187-198 (2005).

* cited by examiner

A.

B.

C.

A.

B.

COMPOSITIONS AND METHODS FOR TREATING ALZHEIMER'S DISEASE AND OTHER TAUOPATHIES

CROSS-REFERENCE TO RELATED APPLICATION(S)

This application claims the benefit of U.S. Provisional Application No. 61/792,009, filed on Mar. 15, 2013, which is hereby incorporated by reference in its entirety.

STATEMENT REGARDING FEDERALLY SPONSORED RESEARCH

This invention was made with Government support under contract MH080378 awarded by the National Institutes of Health. The Government has certain rights in this invention.

FIELD OF THE INVENTION

The present invention pertains generally to compounds, pharmaceutical compositions, and methods of using such compounds and composition to treat or prevent Alzheimer's disease and related tauopathies through the inhibition of USP-9X and/or enhancement of SCF(β-TrCP).

BACKGROUND OF THE INVENTION

Alzheimer's disease (AD) is the leading cause of dementia in the elderly. Although it is well-known that disease progression is associated with formation of amyloid plaques (AP) and neurofibrillary tangles (NFT), memory deficits in AD patients do not correlate well with either AP or NFT burden. Rather, loss of synaptic markers better predicts clinical symptoms and disease progression and suggests that AD is a disease of synaptic failure (Selkoe (2002) Science 298:789-791). Accumulating evidence supports a role for amyloid-β (Aβ as the causative agent in synaptic and spine pathology in AD (Spires et al. (2005) J. Neurosci. 25:7278-7287; Reddy et al. (2008) Trend. Mol. Med. 14:45-53; Selkoe (2008) Brain Res. 192:106-113). Rare genetic mutations cause familial AD by altering the production or metabolism of A-β (Hardy et al. (2002) Science 297:353-356; Holtzman et al. (2011) Sci. Transl. Med. 3:77sr71), the soluble pool of which correlates with disease progression and severity (Selkoe (2008) Behav. Brain Res. 192:106-113). Recent studies have supported tau as a major mediator of Aβ toxicity.

Current treatments for Alzheimer's disease ameliorate symptoms, but fail to halt the progression of the disease. Thus, there remains a need for new treatments that can target key mediators of the pathways that give rise to the pathogenic steps, such as tau hyperphosphorylation, that lead to progression of Alzheimer's disease.

BRIEF SUMMARY OF THE INVENTION

Disclosed herein is a composition for treating or preventing Alzheimer's disease and related tauopathies, the composition comprising a USP-9x inhibitor and a SCF(β-TrCP) enhancer.

Disclosed herein is a composition for treating or preventing Alzheimer's disease and related tauopathies, the composition comprising a USP-9x inhibitor and a SCF(β-TrCP) wherein the USP-9x inhibitor is WP1130 or derivatives thereof.

Disclosed herein is a composition for treating or preventing Alzheimer's disease and related tauopathies, the composition comprising a USP-9x inhibitor and a SCF(β-TrCP) wherein the USP-9x inhibitor is has the structure:

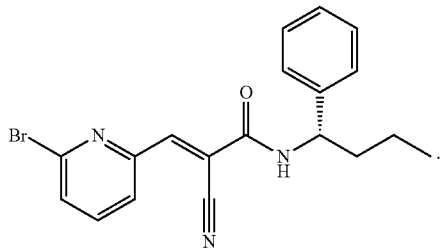 [SMILES: CCC[C@H](NC(=O)/C(C#N)=C/c1cccc(Br)n1)c1ccccc1]

Disclosed herein is a composition for treating or preventing Alzheimer's disease and related tauopathies, the composition comprising a USP-9x inhibitor and a SCF(β-TrCP) wherein the SCF(β-TrCP) enhancer increases the neddylation of Cullin.

Disclosed herein is a method for preventing or treating Alzheimer's disease and related tauopathies in an animal, the method comprising administering to the animal an effective amount of a composition comprising a USP-9x inhibitor and a pharmaceutically acceptable carrier thereof.

Disclosed herein is a method for preventing or treating Alzheimer's disease and related tauopathies in an animal, the method comprising administering to the animal an effective amount of a composition comprising a USP-9x inhibitor and a pharmaceutically acceptable carrier thereof wherein the USP-9x inhibitor is WP1130 or derivatives thereof.

Disclosed herein is a method for preventing or treating Alzheimer's disease and related tauopathies in an animal, the method comprising administering to the animal an effective amount of a composition comprising a USP-9x inhibitor, a SCF(β-TrCP) enhancer, a pharmaceutically acceptable carrier thereof.

Disclosed herein is a kit comprising a USP-9x inhibitor and a pharmaceutically acceptable carrier thereof.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1A-D show genetic interaction between PAR-1 and FAF in the fly retina. FIGS. 1E-H show representative NMJ terminals of the indicated genotypes revealed by anti-horseradish peroxidase (HRP) immunostaining. The genotypes are Mhc-Gal4/+control (FIG. 1E), Mhc-Gal4>FAF$^{EP3520}$ (FIG. 1F), Mhc-Gal4>UAS-PAR-1 (FIG. 1G) and Mhc-Gal4>UAS-PAR-1+FAF$^{EP3520}$ (FIG. 1H) FIG. 1I shows quantification of the total number of boutons per muscle area on muscle 6/7 of A3 in the indicated genotypes.

FIGS. 2A-O show that PAR-1 serves as a common substrate for FAF and Slimb. FIGS. 2A-J show genetic interaction between FAF and Slimb in the retina. FIG. 2K shows western blot analysis of PAR-1 protein levels in the indicated genotypes. FIG. 2L shows double labeling of larval NMJs with anti-horseradish peroxidase (HRP) and anti-p-PAR-1. FIG. 2M shows quantification of p-PAR-1 signals in FIG. 2L and FIG. 2M after normalization with HRP signal. FIG. 2N shows quantification of bouton numbers showing genetic interaction between PAR-1 and Slimb at the NMJ. FIG. 2O shows quantification of bouton numbers showing genetic interactions among Slimb, FAF, and PAR-1 at the NMJ.

FIG. 3A shows western blot analysis showing enhanced in vivo ubiquitination of PAR-1 by Slimb. FIG. 3B shows western blot analysis showing effects of Slimb-WT or Slimb-ΔF on transgene-derived total PAR-1 and p-PAR-1 levels. Actin serves as a loading control. FIG. 3C shows the quantification of the ratio of p-PAR-1/total PAR-1 levels shown in FIG. 3B. FIG. 3D shows an IP experiment showing selective binding of Slimb to PAR-1-WT compared with PAR-1-T408A. FIG. 3E shows In vivo ubiquitination assay showing reduced ubiquitination of PAR-1-T408A compared with PAR-1-WT. FIG. 3F shows the genetic interaction between PAR-1 and Slimb in the retina in each of the indicated genotypes. FIG. 3G shows western blot analysis showing non-responsiveness of PAR-1-T408 protein abundance to Slimb activity. FIG. 3H shows a pulse-chase assay showing differential stability of PAR-1-WT and PAR-1-T408A in HEK293 cells.

FIG. 4A shows the quantification of NMJ boutons showing genetic interaction between LKB1 and PAR-1 or Dlg. N indicates the number of animals analysed. FIG. 4B shows the quantification of NMJ bouton number showing genetic interaction between LKB1 and Slimb or FAF. FIG. 4C shows genetic interaction between LKB and FAF or Slimb in the retina in each of the indicated genotypes. FIGS. 4D-E show western blot analyses showing the effects of LKB1 interaction with Slimb/FAF on PAR-1 and p-PAR-1 levels in adult fly head extracts (FIG. 4D) or third instar larvae body-wall muscle extracts (FIG. 4E).

FIGS. 5A-F show the genetic interaction between APP/Aβ-42 and FAF in the retina. FIGS. 5G-J show representative anti-horseradish peroxidase immunostaining showing larval NMJ morphology. FIGS. 5K-M Quantification of NMJ bouton numbers showing genetic interactions among APP, PAR-1, Slimb, and FAF (FIG. 5K), among Aβ-42, PAR-1, Slimb, and FAF (FIG. 5L), or between APP+PAR-1 and Slimb (FIG. 5M).

FIGS. 6A-D show immunostaining showing dtau localization at third instar larval muscle and NMJ. FIG. 6A shows WT larvae stained with anti-dtau antibody. FIGS. 6B-D show higher magnification images of NMJ boutons double-labelled with anti-dtau and anti-PAR-1 in WT animals FIG. 6B, or labeled with anti-dtau and anti-Dlg in WT FIG. 6C and Da-Gal4>dtau-RNAi animals FIG. 6D. FIG. 6E shows the quantification of NMJ bouton number showing specific genetic interaction between PAR-1 and dtau, but not between hLRRK2 and dtau. FIG. 6F shows the quantification of NMJ boutons showing mediation of the postsynaptic effects of PAR-1 by both Dlg and tau.

FIGS. 7A-B show the quantification of NMJ bouton number showing rescue by htauS2A (FIG. 7A) or dtau-RNAi (FIG. 7B) of the bouton-loss phenotypes induced by manipulations of the expression APP/Aβ-42 or the PAR-1 ubiquitination modifiers. FIG. 7C shows genetic interaction between tau and the modifiers of PAR-1 in the retina. FIG. 7D shows a schematic model depicting possible signaling pathways linking APP/Aβ-42 to synaptic dysfunction and synapse loss seen in AD.

FIG. 8A shows western blot analysis comparing levels of endogenous PAR-1 after Slimb or FAF manipulation using the muscle-specific Mhc-Gal4 driver that did not affect NMJ bouton number, with the level of transgenic PAR-1 in Mhc-Gal4>PAR-1 animals that showed reduced bouton number. FIG. 8B shows western blot analysis of endogenous PAR-1 and p-PAR-1 protein levels or transgenic PAR-1 and p-PAR-1 levels after Slimb or FAF manipulation.

FIG. 9A shows testing for genetic interaction between PAR-1 and CYLD in the fly eye. FIG. 9B shows testing for genetic interaction between PAR-1 and CYLD in the NMJ.

FIG. 10A shows RT-PCR analysis of FAF mRNA levels in wild-type and MhcGal4>FAF RNAi larvae. FIG. 10B shows western blot analysis showing that the FAF RNAi transgene efficiently knocked down the expression of FAF-Myc protein expressed from an hs-FAF-Myc transgene.

FIG. 13A shows western blot analysis showing moderate increase of ubiquitinated forms of PAR-1 in $faf^{FO8}/faf^{BX4}$ mutant thorax extracts. FIG. 13B shows western blot analysis showing a dramatic increase of ubiquitination p-PAR-1 immunoprecipitated from $faf^{FO8}/faf^{BX4}$ mutant fly head extracts.

FIG. 14A shows quantification of data showing the effect of postsynaptic Slimb RNAi on the total number of boutons per muscle area on muscle 6/7 of A3. FIG. 14B shows representative immunostaining with anti-HRP showing NMJ morphology in the indicated genotypes. FIG. 14C shows western blot analysis of endogenous PAR-1, p-PAR-1 and Slimb levels in GMR>Slimb RNAi animals.

FIG. 19A shows double-label experiment showing that phospho-PAR-1 precisely co-localized with Slimb at the larval NMJ. FIG. 19B Double-labeling with anti-HRP and anti-Slimb showing the effects of pre-(elav-Gal4 driven) or post-synaptic (Mhc-Gal4 driven) RNAi knockdown of Slimb on synaptic Slimb signals.

FIG. 22A shows PAR-1 physically interacts with LKB1. FIG. 22B shows representative immunostaining showing larval NMJ morphology in animals overexpressing LKB1 pre- or post-synaptically. FIG. 22C shows quantification of data shown in FIG. 22B.

FIG. 24A shows quantification of larval NMJ bouton number showing genetic interaction between htauM and Slimb or FAF. FIG. 24B shows quantification of NMJ bouton number testing possible genetic interaction between htauM and Dlg variants at the NMJ. FIG. 24C shows western blot analysis of 12E8-positive p-htau level after co-expression of Slimb-WT or Slimb-ΔF in GMR-Gal4>UAS-htauM+UAS-APP-WT background.

FIG. 25A is a western blot showing WP1130 treatment decreases the stability of MARK4. FIG. 25B WP1130 treatment decreased endogenous tau phosphorylation at the MARK sites (recognized by 12E8 antibody).

FIG. 26A shows quantification of the pharmacological effect of WP1130 on the total number of boutons on muscle 6/7 of A3, after normalization with bouton area. Indicated genotype flies were incubated with 0, 2, 5 or 10 μM concentrations of WP1130. FIG. 26B shows western blot analyses showing the effects of WP1130 (10 μM) on PAR-1-Myc levels in third instar larvae body-wall muscle extracts. Values represent normalized PAR-1-Myc levels. Actin serves as loading control. FIG. 26C shows quantification of NMJ bouton number showing rescue by WP1130 (10 μM) of the bouton-loss phenotypes induced by Mhc-Gal4>UAS-htauM or Mhc-Gal4>UAS-htauM+UAS-PAR-1. FIG. 26D Western blot analysis showing reduced 12E8-positive htauM level by WP1130 (10 μM). FIG. 26E shows quantification of NMJ bouton number showing rescue by WP1130 (10 μM) of the bouton-loss phenotypes induced the expression APP/Aβ-42. FIG. 26F shows a model depicting possible signaling pathways linking APP/Aβ-42 to synaptic dysfunction and synapse loss seen in AD

FIG. 28A shows a diagram showing the passive-avoidance test, in which animals were allow to freely moving between the light and dark chambers during habituation. During training, the animals were subjected to electric shock on the foot in the dark chamber. FIG. 28B shows the results of the behavioral experiment in latency time.

DETAILED DESCRIPTION

Figure 1:
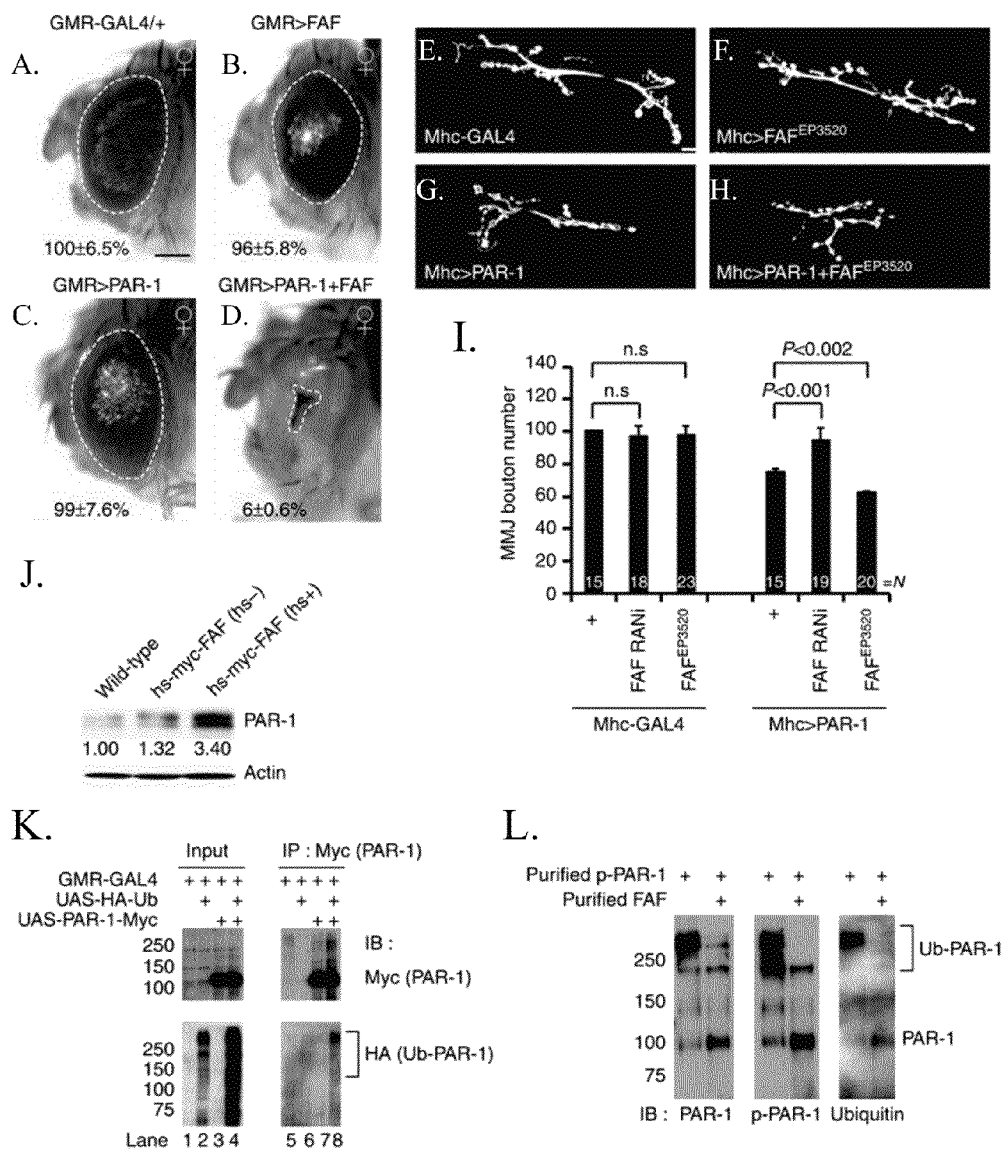
FIGS. 1A-I show that FAF positively regulates PAR-1 activity and protein stability.
FIG. 1J shows western blot analysis of endogenous PAR-1protein level after FAF induction from hs-Myc-FAF.
FIG. 1K shows western blot analysis showing in vivo ubiquitination of PAR-1 in animals co-expressing PAR-1-Myc and HA-Ub.
FIG. 1L shows in vitro deubiquitination assay using affinity-purified, HA-Ub-modified phospho-PAR-1 as the substrate, and affinity-purified FAF as the enzyme.

Although the present invention has been described with reference to preferred embodiments, persons skilled in the art will recognize that changes may be made in form and detail without departing from the spirit and scope of the invention.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein the term "taupathy" may mean but is not limited to a disease characterized by a coexistence of tau-containing intracellular neurofibrillary tangles and β-amyloid plaques. For example, neurofibrillary lesions coexist with β-amyloid plaques in Alzheimer's disease, Creutzfeldt-Jakob disease, dementia pugilistica, Down's syndrome, Gerstmann-Straussler-Sheinker disease, inclusion-body myositis and prion protein cerebral amyloid is angiopathy.

On the other hand, the term "taupathy" may also mean disorders without distinct β-amyloid-containing plaques. Examples of diseases without distinct β-amyloid pathology are frontotemporal dementia (FTD) frontotemporal dementia with parkinsonism linked to chromosome 17 (FTDT-17), Pick's disease, tangle-predominant Alzheimer's disease, corticobasal degeneration, amyotrophic lateral sclerosis/parkinsonism-dementia complex, argyrophilic grain dementia, diffuse neurofibrillary tangles with calcification, Hallevorden-Spatz disease, multiple system atrophy, Niemann-Pick disease, Type C1 progressive subcortial gliosis, progressive supranuclear palsy and subacute sclerosing panencephalitis.

As used herein, the term "analog" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, "homolog" or "homologue" refers to a polypeptide or nucleic acid with homology to a specific known sequence. Specifically disclosed are variants of the nucleic acids and polypeptides herein disclosed which have at least 40, 41, 42, 43, 44, 45, 46, 47, 48, 49, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated or known sequence. Those of skill in the art readily understand how to determine the homology of two proteins or nucleic acids. For example, the homology can be calculated after aligning the two sequences so that the homology is at its highest level. It is understood that one way to define any variants, modifications, or derivatives of the disclosed genes and proteins herein is through defining the variants, modification, and derivatives in terms of homology to specific known sequences.

As used herein, "USP-9x inhibitor" refers to any substance, compound, composition, or agent that inhibits or reduces the expression and/or activity of USP-9x.

As used herein, "a SCF(β-TrCP) enhancer" refers to any substance, compound, composition, or agent that elevates or increases the expression and/or activity and/or concentration of the SCF(β-TrCP) complex or its individual components.

As used herein, "WP1130" means a compound having the formula: $C_{19}H_{18}BrN_3O$ and the structure:

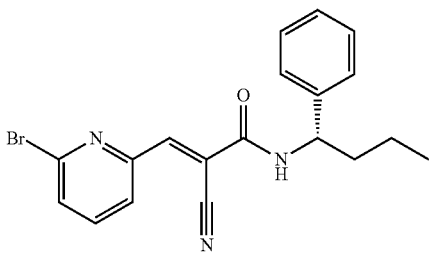 [SMILES: CCC[C@H](NC(=O)/C(C#N)=C/c1cccc(Br)n1)c1ccccc1]

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.)

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to Alzheimer's disease) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "gene therapy" refers to the transfer of heterologous nucleic acid, such as DNA or RNA, into target cells of a human animal, non-human animal, plant or insect having a disorder or condition for which such therapy or treatment is sought. As used herein, gene therapy includes, but is not limited to, the transfer of heterologous nucleic acid, such as DNA, into a virus, which can be transferred to a human animal, non-human animal, plant or insect, with a disorder or condition for which such therapy or treatment is sought. The nucleic acid, such as DNA, is introduced into the selected target cells, such as directly or indirectly, in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that is in some manner a therapeutic product, or which mediates, directly or indirectly, expression of a therapeutic product. Gene therapy also includes, but is not limited to, the delivery of nucleic acid encoding a gene product that replaces a defective gene or supplements a gene product produced by the human animal, non-human animal, or the cell thereof in which it is introduced. The introduced nucleic acid can include, but is not limited to, a nucleic acid encoding a therapeutic compound. The heterologous nucleic acid, such as DNA, encoding the therapeutic product can be modified prior to introduction into the cells of the afflicted host in order to enhance or otherwise alter the product or expression thereof. Gene therapy can also include, but is not limited to, the delivery of an inhibitor or repressor or other modulator of gene expression.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

"Pharmaceutically acceptable excipient or carrier" refers to an excipient that may optionally be included in the compositions of the invention and that causes no significant adverse toxicological effects to the patient. "Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium). An "effective amount" of a USP-9x inhibitor and/or an SCF (β-TrCP) enhancer is an amount sufficient to effect beneficial or desired results, such as an amount that leads to ubiquitination and degradation of MARK, and/or reduces or prevents hyperphosphorylation of tau or PSD-95, and/or reduces or prevents deposition of neurofibrillary tangles, and/or reduces or prevents loss of expression of synaptic markers, and/or reduces or prevents loss of dendritic spines, and/or reduces or prevents loss of synapses. An effective amount can be administered in one or more administrations, applications or dosages.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted). Disclosed herein are compositions for treating or preventing Alzheimer's disease and related tauopathies, the composition comprising a USP-9x inhibitor and a SCF(β-TrCP) enhancer. In a further aspect, the invention disclosed herein relates to compositions useful in methods for treating or preventing Alzheimer's disease and related tauopathies, and pharmaceutical compositions comprising compositions used in the methods.

In one aspect, the compositions are useful in the treatment of Alzheimer's disease and related tauopathies. In certain aspects, compositions disclosed herein are useful in the treatment related tauopathies including but not limited to, Creutzfeldt-Jakob disease, dementia pugilistica, Down's syndrome, Gerstmann-Straussler-Sheinker disease, inclusion-body myositis and prion protein cerebral amyloid is angiopathy, frontotemporal dementia (FTD) frontotemporal dementia with parkinsonism linked to chromosome 17 (FTDT-17), Pick's disease, tangle-predominant Alzheimer's disease, corticobasal degeneration, amyotrophic lateral sclerosis/parkinsonism-dementia complex, argyrophilic grain dementia, diffuse neurofibrillary tangles with calcification, Hallevorden-Spatz disease, multiple system atrophy, Niemann-Pick disease, Type C1 progressive subcortial gliosis, progressive supranuclear palsy, subacute sclerosing panencephalitis, and chronic traumatic encephalopathy.

Disclosed herein are compositions for treating or preventing Alzheimer's disease and related tauopathies, the composition comprising a USP-9x inhibitor. In an aspect, the composition comprises a therapeutically effective amount of a USP-9x inhibitor. In an aspect, the composition comprises a prophylactically effective amount of a USP-9x inhibitor. In an aspect, the amount of inhibitor in the composition is greater than 100 mg/kg. In a further aspect, the amount of inhibitor in the composition is greater than 50 mg/kg. In an aspect, the amount of inhibitor in the composition is greater than 25 mg/kg. In an even further aspect, the amount of inhibitor in the composition is greater than 10 mg/kg. In an aspect, the USP-9x inhibitor acts via ubiquitination and degradation of MARK, and/or reduces or prevents hyperphosphorylation of tau or PSD-95.

Certain embodiments relate to compositions useful in treating or preventing Alzheimer's disease and related tauopathies by providing to a subject in need thereof an effective amount of WP1130 or a derivative thereof, and pharmaceutical compositions comprising compositions used in the methods. In an aspect, the USP-9x inhibitor is WP1130 or a derivative. WP1130, also known as Degrasyn, is known to suppress Bcr/Abl, a JAK2 transducer (without affecting 20S proteasome) and activator of transcription (STAT). Other names for WP 1130 include: 856243-80-6; (S,E)-3-(6-bromopyridin-2-yl)-2-cyano-N-(1-phenylbutyl)acrylamide; QCR-21; CHEMBL1923233; CS-0483; HY-13264; KB-81491; X7509; and (2E)-3-(6-bromopyridin-2-yl)-2-cyano-N-[(1S)-1-phenylbutyl]prop-2-enamide. The structure is as follows:

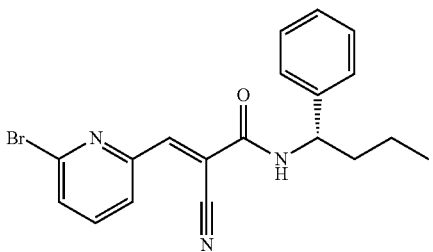

Disclosed herein are compositions for treating or preventing Alzheimer's disease and related tauopathies, comprising a USP-9x inhibitor and/or a SCF(β-TrCP) enhancer. In certain embodiments, the inhibitor is RNA interference (RNAi) targeting USP-9x. In further embodiments, the RNAi is miRNA targeting USP-9x. In still further embodiments the RNAi is siRNA targeting USP-9x. According to certain embodiments, the RNAi is shRNA targeting USP-9x.

It is understood that the nucleic acids sequences of the genes disclosed herein can be used for RNAi or RNA interference. It is thought that RNAi involves a two-step mechanism for RNA interference (RNAi): an initiation step and an effector step. For example, in the first step, input double-stranded (ds) RNA (siRNA) is processed into small fragments, such as 21-23-nucleotide 'guide sequences'. RNA amplification occurs in whole animals. Typically then, the guide RNAs can be incorporated into a protein RNA complex which is capable of degrading RNA, the nuclease complex, which has been called the RNA-induced silencing complex (RISC). This RISC complex acts in the second effector step to destroy mRNAs that are recognized by the guide RNAs through base-pairing interactions. RNAi involves the introduction by any means of double stranded RNA into the cell which triggers events that cause the degradation of a target RNA. RNAi is a form of post-transcriptional gene silencing. In addition to the siRNAs disclosed herein, disclosed are RNA hairpins that can act in RNAi. For description of making and using RNAi molecules see, e.g., Hammond et al., Nature Rev Gen 2: 110-119 (2001); Sharp, Genes Dev 15: 485-490 (2001), Davidson and McCray, Nat Rev Genet. 2011 May; 12(5):329-40, all of which are incorporated herein by reference in their entireties and at least form material related to delivery and making of RNAi molecules. Accordingly, siRNAs can be used to modulate transcription and translation to for example, decrease expression of and thus inhibit the activity of USP-9X.

According to certain embodiments, the invention relates to pharmaceutical compositions for treating or preventing Alzheimer's disease and related tauopathies comprising a USP-9x inhibitor and a SCF(β-TrCP) enhancer. According to certain embodiments, the SCF(β-TrCP) enhancer is present in a therapeutically effective amount. According to further embodiments, the SCF(β-TrCP) enhancer is present in a prophylactically effective amount. According to still further embodiments the SCF(β-TrCP) enhancer is a gene therapy whereby administration of the gene therapy increases the expression or activity of SCF(β-TrCP).

It is known in the art that a key regulator SCF(β-TrCP) is Cullin, the neddlyation of which stimulates SCF(β-TrCP) activity. Accordingly, interventions that upregulate neddlyation of Cullin serve as SCF(β-TrCP) enhancers. There are multiple approaches to increasing neddlyation of Cullin. For example, NEDD8 and the NEDD8 activating enzyme (NAE) increase Cullin neddylation. Therefore overexpression of NEDD8 or NAE, for example, by gene therapy, increases Cullin neddylation and thus is a SCF(β-TrCP) enhancer. Similarly, increasing NAE activity through small molecule activators of NAE increase neddylation and are thus SCF(β-TrCP) enhancers.

CAND1 (culling-associated, neddylation-disassociated1) increases neddylation of Cullin. Accordingly, gene therapy approaches that boost CAND1 expression are SCF(β-TrCP) enhancers. Similarly, small molecule activators of CAND1 are SCF(β-TrCP) enhancers.

A further approach to enhance SCF(β-TrCP) activity is to block the deneddylation of Cullin. COP9 signalosome (CSN) is a Cullin deneddylase and its inhibition results in a increase in Cullin neddylation. Accordingly, reducing CSN expression, such as with RNAi, enhances SCF(β-TrCP). Further, small molecule inhibitors of CSN lead to increased neddylation of Cullin and are thus SCF(β-TrCP) enhancers.

Accordingly, in certain aspects, the disclosed compositions for treating or preventing Alzheimer's disease and related tauopathies comprise a USP-9x inhibitor and a SCF(β-TrCP) enhancer wherein the SCF(β-TrCP) enhancer increases the neddylation of Cullin. In further aspects, the SCF(β-TrCP) enhancer increases the expression or activity of NEDD8 or NAE. In still further aspects, the SCF(β-TrCP) enhancer is a gene therapy that increases expression of NEDD8 or NAE. In yet further aspects, the SCF(β-TrCP) enhancer is a small molecule activator of NAE.

In certain aspects, the SCF(β-TrCP) enhancer increases the neddylation of Cullin by increasing activity and/or expression of CAND1. In further aspects, the SCF(β-TrCP) enhancer increases expression of CAND1 by a gene therapy. In yet further aspects, the SCF(β-TrCP) enhancer increases activity of CAND1 through administration of a small molecule activator.

In certain aspects, the SCF(β-TrCP) enhancer increases the neddylation of Cullin by decreasing Cullin deneddylation. In further aspects, the SCF(β-TrCP) enhancer decreases deneddylation through inhibition of CSN. In further aspects, the SCF(β-TrCP) enhancer inhibits CSN through RNAi targeting CSN. In further aspects, the RNAi is miRNA targeting CSN. In still further aspects, the RNAi is siRNA targeting CSN. According to certain aspects, the RNAi is shRNA targeting CSN. In yet further aspects, the SCF(β-TrCP) enhancer inhibits CSN through administration of a small molecule inhibitor of CSN.

According to certain embodiments, the invention relates to pharmaceutical compositions comprising a USP-9x inhibitor and a SCF(β-TrCP) enhancer. In an aspect, the disclosed pharmaceutical compositions can be provided comprising a therapeutically effective amount of the inhibitor and/or the enhancer, and a pharmaceutically acceptable carrier. The disclosed pharmaceutical compositions can be provided comprising a prophylactically effective amount of the inhibitor and/or the enhancer, and pharmaceutically acceptable carrier.

In practice, the disclosed compositions, or pharmaceutically acceptable salts thereof, can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds known to treat or reduce symptoms of Alzheimer's disease and related tauopathies.

The pharmaceutical carrier employed can be, for example, a solid, liquid, or gas. Examples of solid carriers include lactose, terra *alba*, sucrose, talc, gelatin, agar, pectin, *acacia*, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions disclosed herein comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) and intracerebroventricular administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions disclosed herein suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions disclosed herein suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions disclosed herein can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions disclosed herein can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of cellular function related to depositions of tau, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

Accumulating evidence supports a role for amyloid-β (Aβ as the causative agent in synaptic and spine pathology in. Rare genetic mutations cause familial AD by altering the production or metabolism of A-β, the soluble pool of which correlates with disease progression and severity. Depletion of soluble Aβ in mouse AD models rescued the cognitive deficits. Moreover, synthetic Aβ oligomers or those purified from cultured cells or brain samples can induce neuritic degeneration, neurotransmission defects, and spine loss.

Recent studies have supported tau as a major mediator of Aβ toxicity. Injections of Aβ or crossing an APP transgene into tau transgenic animals promote NFT pathology, and antibody-based removal of Aβ reduced hyperphosphorylated tau and rescued behavioral and pathological dctself0e in a APP/Psn/tau 3×Tg AD mouse model. Moreover, removal of tau relieves Aβ-induced neurotoxicity in culture, and prevents Aβ-induced behavioral deficits in an h-APP Tg mouse model.

It is not clear how tau abnormality arises in AD, but may it be linked to tau hyperphosphorylation. A number of kinases and phosphatases are known to regulate tau phosphorylation. Partitioning defective-1 (PAR-1)/microtubule affinity regulating kinase (MARK) was originally identified in C. elegans for its role in regulating cell polarity. PAR-1 and its mammalian homologue MARK phosphorylate tau and have been implicated in pathogenic deposition of neurofibrillary tangles. In Drosophila models, PAR-1-mediated phosphorylation is required for conferring tau toxicity. Elevation of PAR-1/MARK-mediated tau phosphorylation (at 12E8 sites) was observed in AD patients and mouse AD models Activated Drosophila PAR-1 also directly phosphorylates the postsynaptic density protein 95 (PSD-95) homologue discs large (Dlg), impairing its postsynaptic localization, which might be mechanistically related to the synaptic loss of PSD-95 seen in early stages of AD in patients and mouse models.

The detrimental consequences of deregulation or dysfunction of PAR-1/MARKs entail a stringent control over their activities in vivo. PAR-1/MARK activity can be regulated by phosphorylation, intra-molecular interaction, and inter-molecular interaction. Certain kinases have been implicated in phosphorylating PAR-1/MARKs. For example, phosphorylation by LKB1 and MARKK both positively regulate PAR-1/MARK activity, and LKB1 has been shown to promote PAR-1 activity in AD-related processes. It is not known how the active phospho-PAR-1 (p-PAR-1) generated by LKB1 and/or MARKK action is regulated in vivo.

Protein ubiquitination and deubiquitination play essential roles in cell signaling during development and in tissue maintenance in adults. Defects in this process contribute to disease conditions such as neurodegeneration and cancer. The SCF (Skp_Cul1_F-box) E3 ubiquitin ligase complex is primarily involved in ubiquitinating phospho-substrates, with the F-box-containing subunit recognizing and recruiting phospho-targets. Hence, the SCF complex is particularly important for kinase signaling. One of the well-studied SCF complexes is the Drosophila SCF(Slimb) and its mammalian counterpart SCF(β-TrCP), which contain the F-box proteins Slimb and β-TrCP, respectively, and are critically involved in diverse processes. The effects of ubiquitination on the turnover or activity of target proteins are counteracted by deubiquitinating enzymes.

The compositions disclosed herein are useful for treating, preventing, ameliorating, controlling or reducing the risk Alzheimer's disease and a variety of related tauopathies. Examples of such taupathies include, but are not limited to, Creutzfeldt-Jakob disease, dementia pugilistica, Down's syndrome, Gerstmann-Straussler-Sheinker disease, inclusion-body myositis and prion protein cerebral amyloid is angiopathy, frontotemporal dementia (FTD) frontotemporal dementia with parkinsonism linked to chromosome 17 (FTDT-17), Pick's disease, tangle-predominant Alzheimer's disease, corticobasal degeneration, amyotrophic lateral sclerosis/parkinsonism-dementia complex, argyrophilic grain dementia, diffuse neurofibrillary tangles with calcification, Hallevorden-Spatz disease, multiple system atrophy, Niemann-Pick disease, Type C1 progressive subcortial gliosis, progressive supranuclear palsy, subacute sclerosing panencephalitis, and chronic traumatic encephalopathy.

Thus, provided is a method for treating or preventing Alzheimer's disease and related tauopathies, comprising: administering to a subject at least one disclosed compound; at least one disclosed pharmaceutical composition; and/or at least one disclosed product in a dosage and amount effective to treat the disorder in the subject.

Disclosed herein is a method for preventing or treating Alzheimer's disease and related tauopathies in an animal, the method comprising administering to the animal an effective amount of a composition comprising a USP-9x inhibitor.

In certain aspects, the USP-9x inhibitor is WP1130. In further aspects, the inhibitor is WP1130 or derivatives thereof.

In certain embodiments, the method for preventing or treating Alzheimer's disease and related tauopathies in an animal comprises administering to the animal an effective amount of a composition comprising a compound the formula:

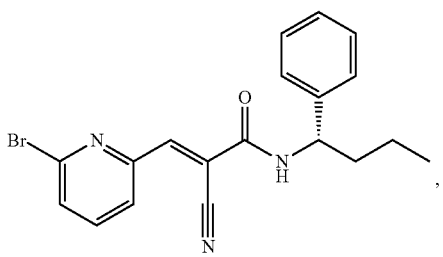

and a pharmaceutically acceptable carrier thereof.

In certain embodiments, the USP-9x inhibitor is RNAi targeting USP-9x. In further embodiments, the USP-9x inhibitor is miRNA targeting USP-9x. In still further embodiments, the USP-9x inhibitor is shRNA targeting USP-9x.

In certain embodiments, the disclosed method is a method for preventing or treating Alzheimer's disease and related tauopathies in an animal, the method comprising administering to the animal an effective amount of a composition comprising a USP-9x inhibitor and further comprising a SCF(β-TrCP) enhancer. In certain aspects, the SCF(β-TrCP) enhancer increases the neddylation of Cullin. In further aspects, the SCF(β-TrCP) enhancer increases the expression or activity of NEDD8 or NAE. In still further aspects, the SCF(β-TrCP) enhancer is a gene therapy that increases expression of NEDD8 or NAE. In yet further aspects, the SCF(β-TrCP) enhancer is a small molecule activator of NAE.

In certain aspects, the SCF(β-TrCP) enhancer increases the neddylation of Cullin by increasing activity and/or expression of CAND1. In further aspects, the SCF(β-TrCP) enhancer increases expression of CAND1 by a gene therapy. In yet further aspects, the SCF(β-TrCP) enhancer increases activity of CAND1 through administration of a small molecule activator.

In certain aspects, the SCF(β-TrCP) enhancer increases the neddylation of Cullin by decreasing Cullin deneddylation. In further aspects, the SCF(β-TrCP) enhancer decreases deneddylation through inhibition of CSN. In further aspects, the SCF(β-TrCP) enhancer inhibits CSN through RNAi targeting CSN. In further aspects, the RNAi is miRNA targeting CSN. In still further aspects, the RNAi is siRNA targeting CSN. According to certain aspects, the RNAi is shRNA targeting CSN. In yet further aspects, the SCF(β-TrCP) enhancer inhibits CSN through administration of a small molecule inhibitor of CSN.

In certain aspects, the animal is a mammal, fish or bird. In a yet further aspect, the mammal is a primate. In a still further aspect, the mammal is a human. In an even further aspect, the human is a patient.

In certain embodiments, the composition is administered in an amount between about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. This dosing regimen can be adjusted to provide the optimal therapeutic response.

In a further aspect, prior to the administering step the patient has been diagnosed with a need for treatment of a Alzheimer's disease or related tauopathies. In a yet further aspect, the disorder is Alzheimer's disease.

In further aspects, prior to the administering step the patient is a high risk for developing Alzheimer's disease or related tauopathies. In yet further aspects, the patient is at high risk for familial Alzheimer's disease. In still further aspects, the patient carries one or more mutations in a gene associated with familial Alzheimer's disease. In further aspects, the patient carries a mutation in presenilin 1, presenilin 2 or amyloid precursor protein (APP).

In a further aspect, a use is administration of the composition in an effective amount. In a yet further aspect, the effective amount is a therapeutically effective amount. In a still further aspect, the effective amount is a prophylactically effective amount. In a still further aspect, prior to use the mammal in need of treatment of Alzheimer's disease and related tauopathies. In a yet further aspect, prior to use the mammal in need of prevention Alzheimer's disease and related tauopathies is identified.

Disclosed herein is a kit comprising a USP-9x inhibitor. In an aspect, the kit further comprises instructions for treatment of Alzheimer's disease and/or related tauopathies.

In an aspect, the inhibitor of the disclosed kit is WP1130. In an aspect, the inhibitor is a derivative of WP1130.

In an aspect, the inhibitor of the disclosed kit is RNA interference. In an aspect, the RNA interference targets USP-9x. In a further aspect, the RNA interference is miRNA targeting USP-9x. In a further aspect, the RNA interference is siRNA targeting USP-9x. In yet a further aspect, the RNA interference is shRNA targeting USP-9x.

Disclosed herein is a kit comprising a USP-9x inhibitor and a SCF(β-TrCP) enhancer. In certain aspects, the disclosed compositions for treating or preventing Alzheimer's disease and related tauopathies comprise a USP-9x inhibitor and a SCF(β-TrCP) enhancer wherein the SCF(β-TrCP) enhancer increases the neddylation of Cullin. In further aspects, the SCF(β-TrCP) enhancer increases the expression or activity of NEDD8 or NAE. In still further aspects, the SCF(β-TrCP) enhancer is a gene therapy that increases expression of NEDD8 or NAE. In yet further aspects, the SCF(β-TrCP) enhancer is a small molecule activator of NAE.

In certain aspects, the SCF(β-TrCP) enhancer increases the neddylation of Cullin by increasing activity and/or expression of CAND1. In further aspects, the SCF(β-TrCP) enhancer increases expression of CAND1 by a gene therapy. In yet further aspects, the SCF(β-TrCP) enhancer increases activity of CAND1 through administration of a small molecule activator.

In certain aspects, the SCF(β-TrCP) enhancer increases the neddylation of Cullin by decreasing Cullin deneddylation. In further aspects, the SCF(β-TrCP) enhancer decreases deneddylation through inhibition of CSN. In further aspects, the SCF(β-TrCP) enhancer inhibits CSN through RNAi targeting CSN. In further aspects, the RNAi is miRNA targeting CSN. In still further aspects, the RNAi is siRNA targeting CSN. According to certain aspects, the RNAi is shRNA targeting CSN. In yet further aspects, the SCF(β-TrCP) enhancer inhibits CSN through administration of a small molecule inhibitor of CSN.

In an aspect, the inhibitor and the enhancer are coformulated. In a further aspect, the inhibitor and the elevator are copackaged. In an aspect, the kit further comprises instructions for treatment of Alzheimer's disease and related tauopathies.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in °C. or is at ambient temperature, and pressure is at or near atmospheric.

The UAS-PAR-1-WT, UAS-PAR-1-T408A, UAS-PAR-1 RNAi, UAS-LKB1-WT, UAS-LKB1-KD, UAS-LKB1 RNAi, UAS-Dlg-WT-GFP, UAS-Dlg-SA-GFP, UAS-Dlg-SD-GFP, UAS-htauM and UAS-htauS2A were described before[10, 21]. UAS-HA-Ub was provided by Dr. K Chung[47], UAS-Slimb-WT by Dr. F Rouyer[48], UAS-LKB1-GFP by Dr. D. St Johnston[49], UAS-Myc-Slimb-ΔF by Dr. J Jiang[50], UAS-Ago-WT and UAS-Ago-□F by Dr. K Moberg[25], UAS-A□-42 by Dr. K Iijima-Ando[26], UAS-CYLD 20 by Dr. X Tian, fafBX4, fafF08 and hs-Myc-FAF by Dr. J Fischer[24]. The Mhc-Gal4 driver was provided by Dr. T Littleton. The UAS-FAF RNAi lines were obtained from Vienna *Drosophila* RNAi Center (VDRC). The FAFEP381, FAFEP3520, UAS-APP-WT, UAS-Slimb RNAi and GMR-Gal4 lines were obtained from Bloomington *Drosophila* Stock Center.

For immunohistochemistry, third instar lavae were selected, dissected in PBS, fixed in 4% formaldehyde (Ted Pella) in PBS for about 15 minutes and washed 3× in 0.1% Triton X-100 in PBS. The primary antibodies used were: anti-PAR-1 (1:10,000), anti-phospho-PAR-1 (1:1,000); anti-Slimb (1:1,000); anti-Dlg (4F3) (1:50, Hybridoma bank, University of Iowa); anti-GFP (1:8,000, Abcam); anti-dtau (1:3). Primary antibody incubation was performed at 4° C. overnight. All secondary antibodies (Molecular Probes) and Texas Red or FITC-conjugated anti-HRP (Jackson ImmunoResearch Laboratories) were used at 1:200 and incubated for about 2 hours at room temperature. Laval preparations were mounted in SlowFade Antifade kit (Invitrogen). Confocal images were collected from Leica confocal microscopes SP2 and SP5 equipped with 40× or 100× inverted NX oil lens. Leica application Suite Advanced Fluorescence software was used to capture, process and analyze images. Analysis of the NMJ was performed essentially as described[51]. All crosses for genetic interaction studies in the NMJ were performed at 25° C.

Transfection of HEK 293T cells was performed using 1 μg pCDNA-PAR-1-WT-Myc or PAR-1-T408A construct. To generate the pCDNA-PAR-1-WT-Myc or pCDNA-PAR-1-T408A-Myc constructs, the corresponding cDNA inserts were cloned into the pCDNA3.1 vector (Invitrogen).

For co-immunoprecipitation (co-IP) experiments, 70 mg frozen fly heads expressing UAS-PAR-1-WT-Myc or UAS-PAR-1-T408A-Myc transgene driven by GMR-Gal4 were collected. In the case of LKB1 IP, 50 third instar larvae of lkb1x5 mutant genotype or those expressing a UAS-LKB1-GFP transgene driven by Mhc-Gal4 were dissected. They were homogenized in IP buffer (50 mM Tris-HCl pH 8.0, 1% Triton X-100, 150 mM NaCl, 2 mM Na3VO4, 10 mM NaF, 60 mM □-glycerolphosphate, 10% glycerol, protease inhibitors, 50 μM MG132), and then centrifuged at 12,000 g for 30 minutes at 4° C. Supernatants were pre-cleared by incubation with protein G agarose (Pierce) for 1 hour at 4° C. and then incubated with the indicated IP antibodies for 4 hour at 4° C., followed by incubation with protein G Agarose for 3 hours at 4° C. Beads were washed eight times with the IP buffer or PBS and boiled in SDS sample buffer. The samples were subjected to gel electrophoresis and Western blot analysis.

For Western blot analysis, the primary antibodies used were: anti-PAR-1 (1:8,000), anti-phospho-PAR-1 (1:1,000); anti-HA (1:2,000, Sigma); anti-Myc (1:1,000, Millipore); anti-GFP (1:2,000, Abcam); anti-Dlg (4F3) (1:1,000, Hybridoma bank, University of Iowa); 12E8 (1:8,000); anti-Actin (1:40,000, Sigma); anti-Gapdh (1:3,000, Abcam).

To perform the ubiquitination assay in vivo, 100 frozen fly heads of GMR-Gal4>PAR-1-WT-Myc+HA-Ubi or faf$^{BX4}$/faf$^{F08}$ genotypes were collected and homogenized in the IP buffer (50 mMTris-HCl pH 8.0, 0.1% NP40, 150 mM NaCl, 2 mM Na$_3$VO$_4$, 10 mM NaF, 60 mM β-glycerolphosphate, 10% glycerol and protease inhibitors) and centrifuged at 12,000 g for 30 min at 4° C. Supernatant was incubated with anti-PAR-1 or anti-p-PAR-1 antibody and then with protein G agarose or EZview Red Anti-c-Myc Affinity Gel (Sigma) overnight at 4° C. Beads were washed six times with PBS and boiled in SDS sample buffer.

The p-PAR-1 proteins used as substrate were affinity purified from 50 mg frozen adult fly heads of GMR-Gal4>PAR-1-WT-Myc+HA-Ub genotype, using an anti-p-PAR-1 antibody. The FAF proteins used as the deubiquitinating enzyme were affinity purified with anti-Myc antibody from 50 mg hs-Myc-FAF fly heads collected after hs for 1 h at 37° C. and then stabilized for 2 h at 25° C. To perform the in vitro deubiquitination assay, reactions were performed at 25° C. for 2 h in the deubiquitination buffer (150 mM NaCl, 50 mM Tris-HCl, pH 7.5, 10 mM MgCl$_2$, 1 mM ZnCl$_2$ and 1 mMDTT). The reaction mixtures were stopped by the addition of SDS-PAGE sample loading buffer and boiled at 95-100° C. for 5 min, before subjected to western blot analysis.

Either WP1130 (Selleck Chemicals) or DMSO (Sigma) was added to fly food at 2, 5 or 10 μM concentrations. Feeding third instar larvae were collected from the drug-containing food and dissected in PBS. Besides Mhc-GAL4>UAS-APP, which were raised at 29° C., all flies were raised at 25° C.

Fly eye sizes were measured on multiple samples (n>15) from both control and experimental genotypes using the NIH ImageJ software. Average eye size was presented as a normalized percentage of control eye size. We performed two-tailed unpaired Student's t-test to analyze the significance of differences between two groups. Quantification of NMJ bouton number was performed according to previously described protocols (Lee et al., 2010). NMJ bouton number was normalized by muscle area at muscle 6/7 in abdominal segment A3. The experimental genotypes were normalized relative to the control genotype.

To identify novel regulators of PAR-1, a genetic screen for modifiers of a degeneration phenotype caused by GMR-Gal4>PAR-1 in the retina was performed[6]. A strong modifier that came out of this screen was FAF. A FAF-overexpressing EP line (EP381), which alone caused a mild rough eye phenotype, likely due to its moderate upregulation of endogenous PAR-1 protein level (FIG. 8; data not shown), caused a dramatic reduction of eye size when introduced into GMR-Gal4>PAR-1 background (FIG. 1a-1d). This effect of FAF is specific, as the co-expression of a different deubiquitinating enzyme CYLD[20] failed to modify the GMR-Gal4>PAR-1 phenotype (FIG. 9a). Conversely, introduction of a FAF RNAi transgene, which was effective in knocking down FAF mRNA and protein expression (FIG. 10), partially suppressed GMR-Gal4>PAR-1 effect (FIG. 11).

The functional interaction between PAR-1 and FAF in a different context was also tested. When overexpressed at the postsynapse of the larval neuromuscular junction (NMJ), Mhc-Gal4>PAR-1 exerted synaptic toxicity as shown by a marked loss of boutons[21]. Although FAF overexpression or FAF-RNAi alone had no discernible effect on NMJ synapse morphology, which is likely due to the alterations of endogenous PAR-1 level not reaching a threshold level required for toxicity (FIG. 8), in Mhc-Gal4>PAR-1 background FAF-RNAi rescued the loss of boutons formed on muscle 6/7, whereas FAF overexpression showed significant enhancement (FIG. 1e-1i). Muscle fiber sizes were not affected under these conditions (data not shown). In comparison, the co-expression of CYLD failed to modify the effect of PAR-1 at the NMJ (FIG. 9b), supporting FAF as a positive regulator of PAR-1.

Figure 12:
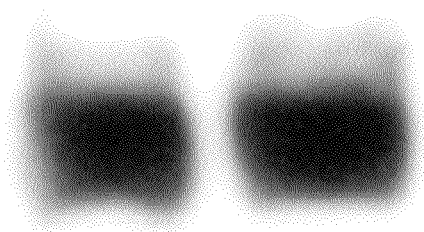
FIG. 12 is a western blot analysis showing that a control deubiquitinating enzyme CYLD did not significantly affect PAR-1 protein level.
Figure 12:
Figure 13:
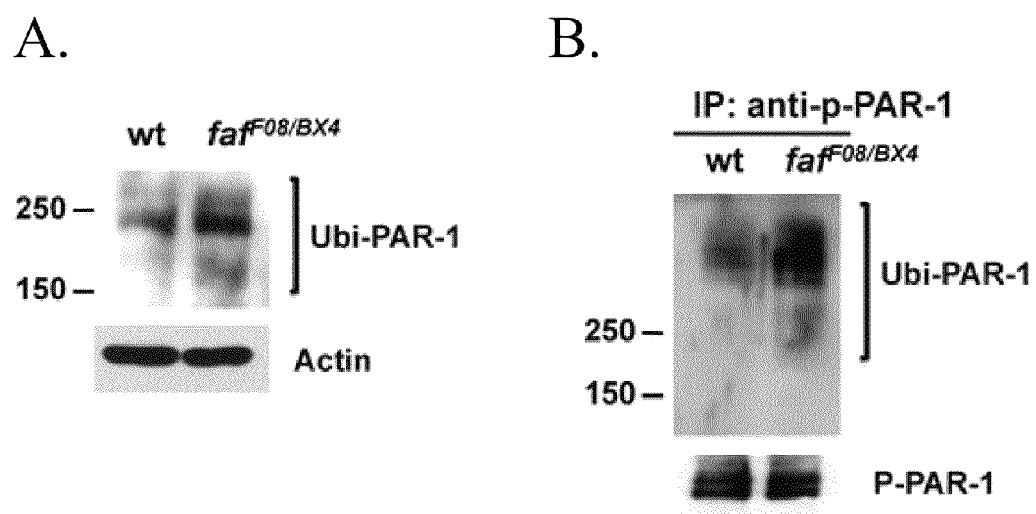
FIGS. 13A-B show that ubiquitinated forms of PAR-1 and p-PAR-1 accumulate in faf mutant.

Ubiquitin specific protease 9X (USP9X), the putative mammalian homolog of FAF, was previously identified as a binding partner of MARK4[22,23], but the functional effect of this interaction was not well defined. Using an hs-FAF-myc transgene[24], it was found that endogenous PAR-1 level was dramatically increased after heat shock (hs+) (FIG. 1j). In contrast, the overexpression of CYLD failed to alter PAR-1 level (FIG. 12). To test whether FAF acts as a deubiquitin enzyme of PAR-1, whether PAR-1 is normally ubiquitinated in vivo was tested. UAS-PAR-1-myc and UAS-HA-Ubiquitin (Ub) were co-expressed in the eye. Transgenic PAR-1 was then subjected to immunoprecipitation (IP) with anti-Myc and its ubiquitination status tested by western blotting with anti-HA. A smear of HA immunoreactivity was detected in PAR-1 IP (FIG. 1k), indicating poly-ubiquitination of PAR-1 in vivo. Moreover, in faf mutant tissue extracts moderately increased ubiquitination of PAR-1 was observed (FIG. 13a), and the effect was more dramatic when p-T408-PAR-1 (FIG. 13b), which corresponds to an activated form of PAR-1[10], was analyzed (FIG. 13). These data support p-PAR-1 as a physiological substrate of FAF. To test whether FAF directly de-ubiquitinates PAR-1, affinity-purified FAF and HA-Ub-labeled PAR-1 were used in an in vitro reaction. FAF clearly reduced poly-ubiquitinated PAR-1 level in vitro (FIG. 1l), supporting that FAF directly deubiquitinates PAR-1.

Figure 14:
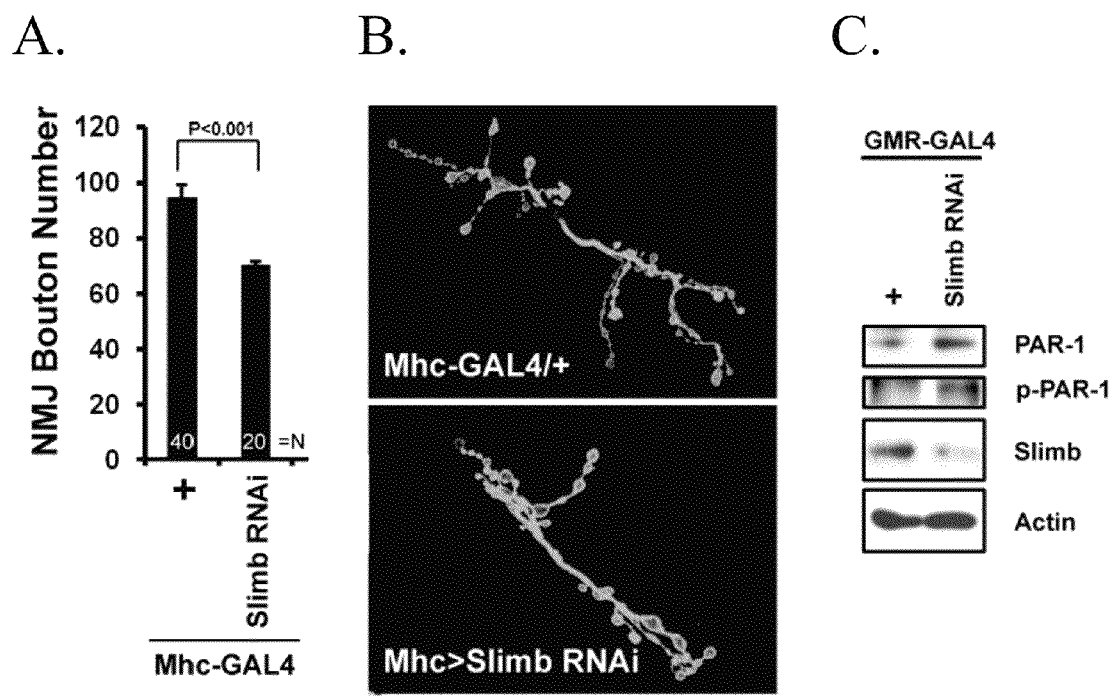
FIGS. 14A-C show the effects of inhibition of Slimb by RNAi on NMJ bouton number.

Based on the assumption that the E3 for PAR-1 would exhibit strong functional interaction with FAF, genetic interaction tests were performed between FAF and candidate E3s for whom gain-of-function or loss-of-function alleles were available. One strong interacting gene was Slimb. Inhibition of Slimb expression using a Slimb-RNAi transgene, which efficiently knocked down Slimb protein expression (FIG. 14c), resulted in increased endogenous PAR-1 or transgenic PAR-1 protein levels (FIG. 14; Fig, s1b) and induced NMJ and eye phenotypes similar to that caused by PAR-1 overexpression (FIG. 2c, 14). Moreover, while co-overexpression of a wild-type Slimb transgene with FAF(EP381) had roughly the same effect (FIG. 2g) as overexpression of FAF(EP381) alone (FIG. 2f), co-expression of a Slimb RNAi transgene with FAF(EP381) resulted in dramatically reduced eye size (FIG. 2h), similar to that seen after PAR-1 and FAF(EP381) co-expression (FIG. 1d). Co-expression of FAF(EP381) and Slimb-ΔF, a dominant-negative form of Slimb[14], also caused eye size reduction, albeit less dramatic than FAF(EP381)/Slimb RNAi co-expression, and the resulting animals exhibited dark patches of necrotic tissues not seen in animals expressing either transgene alone (FIG. 2i). Supporting the specificity of FAF and Slimb interaction, Archipelago (Ago), another F-box component of SCF[25], did not interact with FAF (FIG. 15), and Slimb did not exhibit obvious interaction with CYLD (FIG. 16).

To verify that the genetic interaction between Slimb and FAF was mediated by PAR-1, a PAR-1-RNAi transgene, whose efficiency was characterized before[21], was co-expressed. This resulted in suppression of the synthetic toxicity between FAF and Slimb-ΔF (FIG. 2j) or between FAF and Slimb-RNAi (FIG. 17), suggesting that FAF and SCF(Slimb) both acted on PAR-1. If PAR-1 were a common target through which deregulated Slimb and FAF activities resulted in eye degeneration, altered endogenous PAR-1 protein levels would be expected under those conditions. Indeed, FAF (EP381)/Slimb-ΔF co-expression led to a significant increase of PAR-1 protein level, whereas FAF(EP381)/Slimb-WT co-expression led to a modest decrease (FIG. 2k).

As shown in FIG. 2l, p-PAR-1 was present at low levels in the postsynaptic membrane in wild type NMJ, as reported before[21]. In animals co-expressing FAF and Slimb-ΔF, the level of p-PAR-1 was significantly increased (FIG. 2m, 2n). The specificity of this p-PAR-1 staining is supported by the significant increase of staining signals in animal overexpressing LKB1 (FIG. 18), the kinase responsible for PAR-1 T408 phosphorylation[10]. The effect of FAF and Slimb-ΔF co-expression was relatively specific for PAR-1, as the level of another phospho-protein, p-S6K, was not changed (data not shown).

Figure 19:
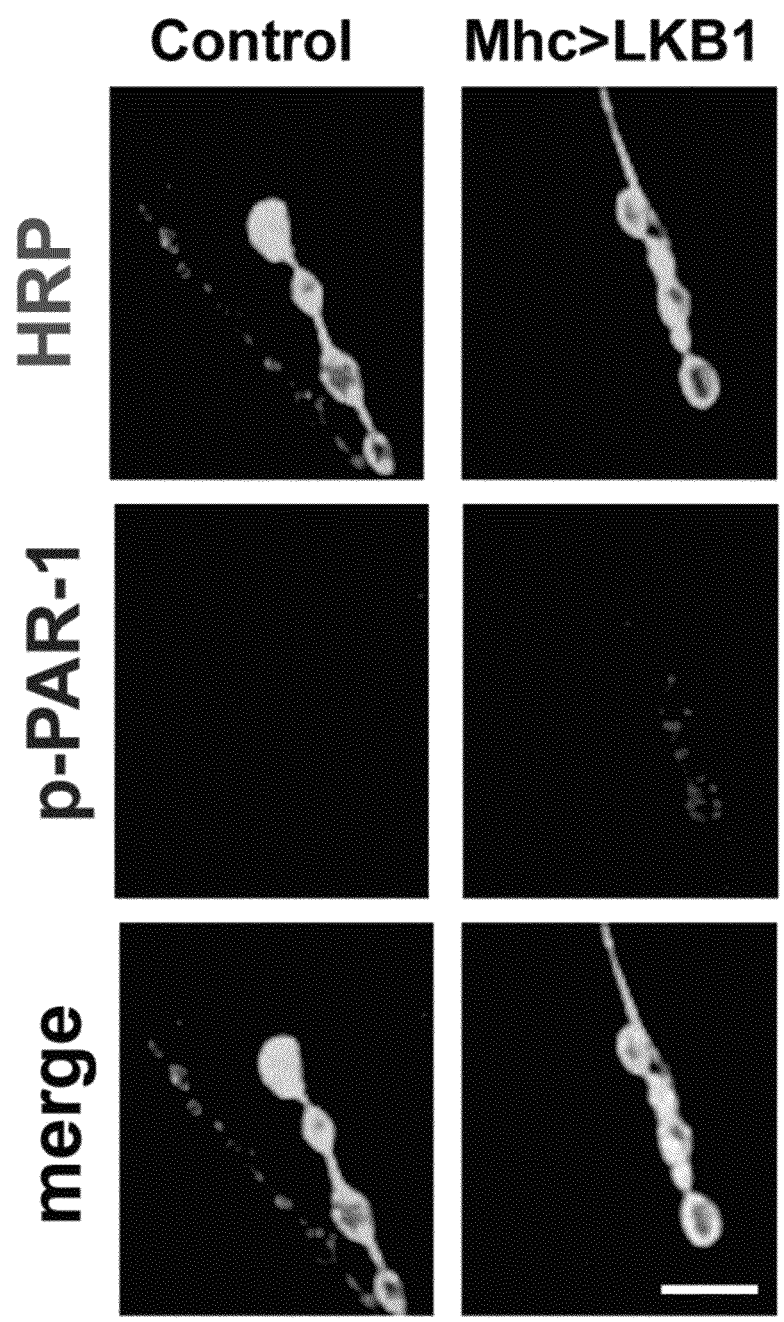
FIGS. 19A-B show that slimb expression is more enriched at the postsynaptic compartment.

To test for a functional link between PAR-1 and Slimb in NMJ synaptic morphogenesis, whether p-PAR-1 co-localized with Slimb was examined. Slimb formed punctate structures that colocalized with p-PAR-1 at the NMJ (FIG. 19). The Slimb-positive signals were dramatically reduced when Slimb was knocked down postsynaptically in Mhc-Gal4>UAS-Slimb RNAi, but only mildly reduced when Slimb was knocked down presynaptically in elav-Gal4>UAS-Slimb RNAi (FIG. 19). This result, together with the significant loss of boutons in Mhc-Gal4>UAS-Slimb-RNAi but not elav-Gal4>UAS-Slimb-RNAi animals (FIG. 14; data not shown), suggested that like PAR-1[21], Slimb plays a more prominent role at the postsynapse.

The NMJ was used to further investigate the relationships among Slimb, FAF, and PAR-1. Postsynaptic overexpression of PAR-1 resulted in ~40% reduction of NMJ boutons (FIG. 2o), an effect rescued by the co-expression of Slimb-WT but enhanced by Slimb-ΔF (FIG. 2o). Dlg was previously shown to be a key substrate mediating the effect of PAR-1 on synaptic morphology, and it is delocalized from the postsynapse by PAR-1[21]. The effect of PAR-1 overexpression on Dlg localization was rescued by Slimb-WT (FIG. 20), consistent with Slimb negatively regulating PAR-1 function. Moreover, whereas postsynaptic expression of either FAF(EP381) or Slimb-ΔF had no obvious effect on NMJ bouton number, presumably due to their moderate effects on endogenous PAR-1 level (FIG. 8a), their co-expression resulted in an ~40% loss of boutons, which was blocked by PAR-1 RNAi (FIG. 2p). These results are consistent with FAF and Slimb playing antagonistic roles in regulating the abundance of PAR-1 protein. Deregulation of this process could lead to the accumulation of activated p-PAR-1 and ensuing synaptic toxicity.

The genetic and biochemical evidence presented so far are consistent with SCF(Slimb) directly targeting PAR-1. To test this possibility, the in vivo ubiquitination assay as described in FIG. 1k was used to examine the effect of Slimb on PAR-1 ubiquitination. Overexpression of Slimb led to increased PAR-1 ubiquitination (FIG. 3a). The effects of Slimb-WT and Slimb-ΔF on the steady-state levels of p-PAR-1 and total PAR-1 expressed from a UAS-PAR-1 transgene were also examined. Slimb-WT decreased, whereas Slimb-ΔF increased, the ratio of p-PAR-1/total PAR-1 (FIG. 3b, c), suggesting that SCF(Slimb) preferentially promotes the degradation of p-PAR-1. Consistently, endogenous p-PAR-1 level was increased by Slimb RNAi (FIG. 14). In co-IP experiments using fly head extracts prepared from animals expressing PAR-1-WT or PAR-1-T408A mutant in the eye, PAR-1-WT but not PAR-1-T408A interacted with endogenous Slimb, supporting that Slimb preferentially recognizes p-T408-PAR-1 (FIG. 3d). This is consistent with role of the F-box subunit of SCF in recognizing and recruiting phospho-targets[13]. Correlated with decreased binding of PAR-1-T408A to Slimb, the in vivo ubiquitination of PAR-1-T408A was greatly diminished compared to PAR-1-WT (FIG. 3e). Furthermore, unlike PAR-1-WT, whose eye phenotype and steady-state level were negatively regulated by Slimb, PAR-1-T408A was no longer responsive to Slimb (FIG. 3f, g).

To further demonstrate that SCF(Slimb) targets p-T408 PAR-1 for ubiquitination and degradation, pulse-chase experiments were performed in HEK293 cells transfected with myc-tagged PAR-1-WT or PAR-1-T408A and in the presence of the translation inhibitor cycloheximide (CHX). Whereas PAR-1-WT was gradually degraded during the chase period in a proteasome-dependent manner, PAR-1-T408A remained stable (FIG. 3h). Collectively, these data demonstrate that SCF(Slimb) targets p-PAR-1 for ubiquitination and degradation.

LKB1 phosphorylates PAR-1 at the T408 site[10]. The localization and biochemical interaction of LKB1 with PAR-1 was examined in vivo using an LKB1-GFP transgene. LKB1-GFP clearly localizes to the NMJ synapse when expressed postsynaptically (FIG. 21), and LKB1-GFP co-IPs with endogenous PAR-1 (FIG. 22a). Next, the relationships among LKB1, Slimb, and PAR-1 at the NMJ was tested. Like PAR-1, LKB1 induced a strong bouton-loss phenotype when overexpressed postsynaptically (FIG. 4a, 22b, 22c). This effect was blocked by PAR-1 RNAi (FIG. 4a), consistent with LKB1 being an upstream activating kinase for PAR-1[10]. Previous studies established Dlg as a key substrate mediating the postsynaptic effects of PAR-1 at the NMJ, with the phosphorylation by PAR-1 negatively regulating the synaptic localization and function of Dlg[21]. Co-expression of Dlg-SA, which is no longer phosphorylated by PAR-1 and can protect against PAR-1-induced synaptic toxicity[21], effectively blocked LKB1 overexpression-induced bouton loss (FIG. 4a). Dlg-WT also showed some protective effect, albeit weaker than Dlg-SA, whereas the phospho-mimetic Dlg-SD had no effect (FIG. 4a). LKB1 thus positively regulates PAR-1 at the postsynapse.

Possible functional interactions among LKB1, Slimb, and FAF at the NMJ were tested next. The bouton-loss phenotype of LKB1 overexpression was effectively rescued by Slimb-WT or FAF RNAi, but enhanced by Slimb-ΔF or FAF (FIG. 4b). The genetic interaction between LKB1 and Slimb in the retina was also tested. Whereas overexpression of LKB1 or Slimb-RNAi each resulted in slight roughness of the eye, their co-expression caused necrosis and a further reduction of eye size (FIG. 4c), supporting their genetic interaction. The relationship between LKB1 and FAF was also examined. The co-expression of LKB1 and FAF led to dramatically reduced eye size (FIG. 4c). Thus, LKB1 and FAF both positively regulate PAR-1, and the overexpression of FAF may enhance LKB1 overexpression effects through the stabilization of p-PAR-1 generated by LKB1.

To gather biochemical evidence that LKB1 and Slimb/FAF work cooperatively in a phospho-dependent ubiquitination and degradation mechanism to regulate PAR-1, PAR-1 protein levels were examined in animals co-expressing LKB1 and Slimb variants or FAF-RNAi. The co-expression of Slimb-WT or FAF-RNAi with LKB1 synergistically reduced endogenous PAR-1 and p-PAR-1 levels, whereas Slimb-RNAi had opposite effects (FIG. 4d, 4e), consistent with LKB1 and Slimb/FAF regulating phospho-dependent ubiquitination and degradation of PAR-1.

The LKB1/PAR-1 axis mediates the toxicity of APP in the retina[10]. Overexpression of FAF had a mild effect, and wild type human APP had no effect on eye size or morphology (FIG. 5b, d). However, their co-expression resulted in significant roughness and eye size reduction (FIG. 5e). Overexpression of Aβ-42 alone caused a slight roughness and eye size reduction, as reported[26], but a significant enhancement was observed upon FAF co-expression (FIG. 5c, f). Thus, the PAR-1 deubiquitinating enzyme FAF influences the toxicity of APP/Aβ-42 in the retina.

Figure 23:
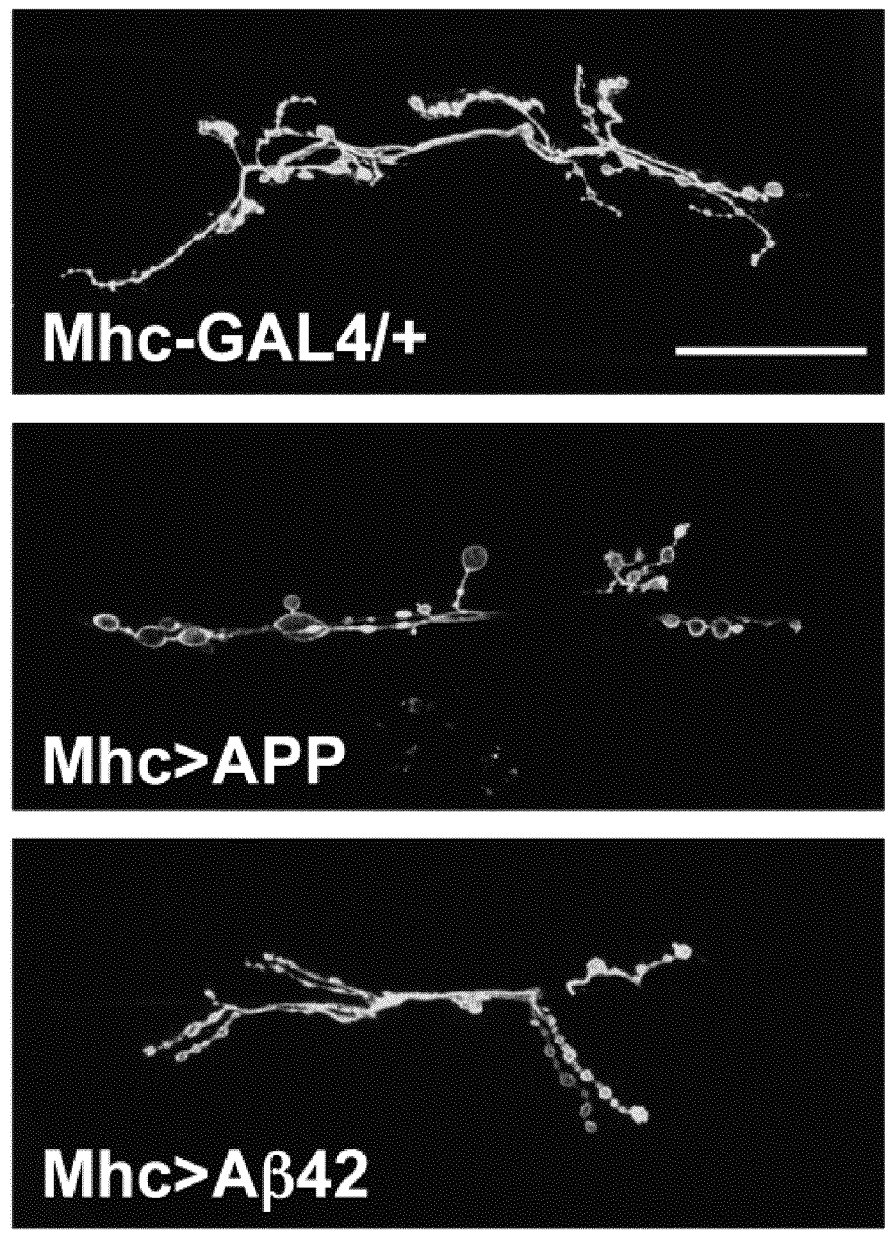
FIG. 23 shows postsynaptic overexpression of APP or Aβ42 leads to a decrease in NMJ bouton number.

AD is increasingly being recognized as a synaptic failure, and accumulating evidence implicate Aβ-42 in causing synaptic toxicity through a postsynaptic mechanism[27,28]. The potential postsynaptic toxicity of APP or Aβ-42 has not been established in Drosophila. Postsynaptic overexpression of APP or Aβ-42 at the NMJ caused ~20% reduction of bouton number (FIG. 23). This effect was rescued by knocking down PAR-1 or FAF, but exacerbated by inhibiting Slimb via Slimb-ΔF (FIG. 5k). Similarly, overexpression of Aβ-42 postsynaptically also caused a reduction of bouton number, and this effect was rescued by Slim-WT, PAR-1-RNAi, or FAF-RNAi (FIG. 5l).

PAR-1 exhibits enriched accumulation at the postsynaptic membrane of the NMJ synapses, where it critically regulates synapse morphology and function'. Postsynaptic co-expression of APP and PAR-1 caused a more severe loss of boutons (FIG. 5h, m), an effect rescued by co-expressing Slimb-WT but not Slimb-ΔF (FIG. 5i, m). Thus, regulation of PAR-1 by SCF(Slimb) critically mediates the toxicity of APP/Aβ-42 at the postsynapse.

To test whether Drosophila tau (dtau) might mediate the postsynaptic toxicity of APP/Aβ-42, postsynaptic expression at the NMJ was also tested. Using a well-characterized dtau antibody', dtau was relatively enriched at the NMJ and colocalized with PAR-1 (FIG. 6a, b), which was predominantly localized to the postsynapse[21], and with Dlg (FIG. 6c), a known postsynaptic marker. This synaptic localization of dtau was eliminated in dtau-RNAi animals (FIG. 6d).

The bouton-loss phenotype caused by postsynaptic PAR-1 was partially suppressed by dtau-RNAi (FIG. 6e). This effect was specific, as the bouton-loss phenotype caused by postsynaptic overexpression of LRRK2[32], was not affected by dtau-RNAi (FIG. 6e). To test whether direct phosphorylation of dtau by PAR-1 might underlie their postsynaptic interaction, a non-phosphorylatable form of human tau with the PAR-1 target sites mutated (htauS2A)[6] was used. Like dtau-RNAi, htauS2A overexpression alone had no obvious effect on synapse morphology. However, its co-expression partially suppressed the effects of postsynaptic PAR-1 but not LRRK2 (FIG. 6f,7a). In comparison, h-tau R406W (htauM), a pathogenic form of tau associated with tauopathy, caused a severe bouton-loss phenotype when overexpressed alone (FIG. 6f), which was partially rescued by Slimb-WT or FAF-RNAi (FIG. 24a), but exacerbated by PAR-1 co-expression (FIG. 6f).

As mentioned earlier, Dlg was previously identified as a substrate of PAR-1 that mediates some of the effects of PAR-1 on postsynaptic morphology and function'. The incomplete rescue by Dlg-SA of PAR-1 overexpression-induced toxicity led to the proposal that there are other key synaptic targets of PAR-1[21]. To test whether Dlg and dtau might both function downstream of PAR-1 at the postsynapse, Dlg-SA and htauS2A were co-expressed in PAR-1 overexpression background. This resulted in a complete rescue of PAR-1 overexpression effect (FIG. 6f). Dlg and dtau appeared to act independently, as suggested by the inability of Dlg-WT or Dlg-SA to rescue the bouton-loss phenotype caused by htauM (FIG. 24b). These results implicate both tau and Dlg as downstream effectors in mediating the postsynaptic effects of PAR-1.

The role of dtau in mediating the toxic effects of APP/Aβ-42 and the modifiers of PAR-1 identified above was next tested. The bouton-loss phenotypes caused by the postsynaptic overexpression of APP, LKB1, or the co-expression of FAF and Slimb-ΔF were all effectively suppressed by the co-expression of htauS2A (FIG. 7a) or dtau-RNAi (FIG. 7b). These results support that postsynaptic dtau, and in particular its phosphorylation by PAR-1, plays a critical role in mediating the synaptic toxicity of APP/Aβ-42.

The extent to which dtau might mediate the toxicity of APP/Aβ-42 and the modifiers of PAR-1 in the retina was also assessed. The eye phenotype caused by FAF/Slimb-ΔF co-expression was significantly attenuated by added expression of htauS2A, but severely exacerbated by the addition of htauM (FIG. 7c). Moreover, the exacerbated toxicity caused by htauM and FAF/Slimb-ΔF synergy was partially relieved by PAR-1-RNAi, consistent with their genetic interaction requiring PAR-1-directed tau phosphorylation (FIG. 7c). At the biochemical level, as reported before', APP promoted tau phosphorylation at the PAR-1 target sites (FIG. 24c). This effect was attenuated by Slimb-WT but enhanced by Slimb-ΔF (FIG. 24c), supporting a critical role of SCF(Slimb)-mediated PAR-1 regulation in the induction of tau phosphorylation by APP. Together, these results support a key role of posttranslational PAR-1 regulation in modulating tau-mediated APP/Aβ-42 toxicity.

Figure 26:
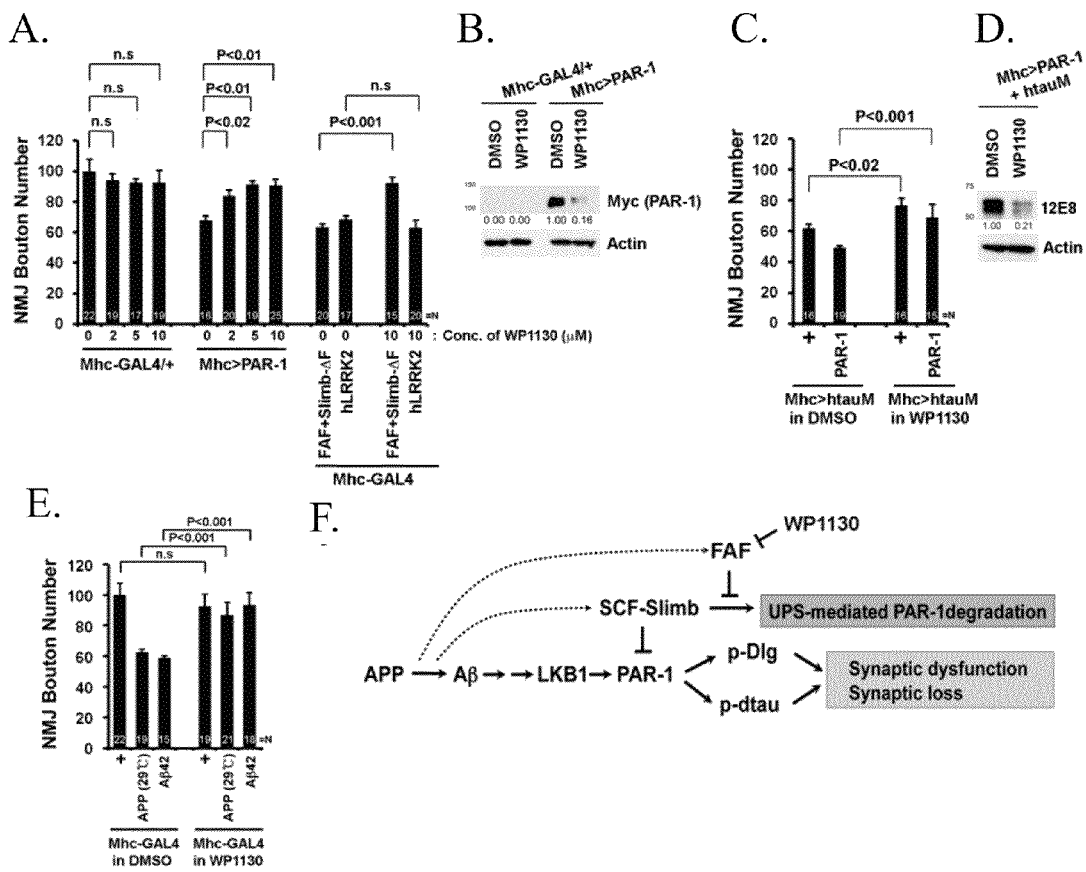
FIGS. 26A-F show pharmacological rescue of postsynaptic toxicity of PAR-1 by small-molecule WP1130.

To investigate whether WP1130 may act as an inhibitor of FAF to control PAR-1 activity in vivo, Mhc-Gal4>PAR-1 and control Mhc-Gal4/+animals were fed with fly food containing WP1130 or DMSO alone. Compared with DMSO-only treatment, WP1130 treatment was highly effective in preventing the loss of NMJ bouton number caused by overexpression of PAR-1 and in reducing PAR-1 protein level (FIG. 26 a,b). WP1130 also blocked synaptic-loss phenotype caused by postsynaptic co-expression of FAF and Slimb-ΔF but not the expression of LRRK2 (FIG. 26 a), supporting that WP1130 acts by preventing FAF activity. Given the potent effect of WP1130 in modulating PAR-1 protein level, whether WP1130 would affect the phosphorylation of tau was tested. It was found that the severe bouton-loss phenotype caused by the co-expression of PAR-1 and htauM was partially suppressed (FIG. 26c) and htau phosphorylation at 12E8 sites was dramatically decreased by WP1130 treatment, as compared to DMSO treatment (FIG. 26d). Moreover, we found that the bouton-loss phenotype caused by the postsynaptic toxicity of APP/Aβ-42 was also effectively suppressed by WP1130 (FIG. 26e). Taken together, these data support that WP1130 can prevent the synaptic toxicity caused by the disease-causing agents APP/Aβ-42 and the activation of PAR-1/MARK, and might offer an alternative approach to reducing pathological tau phosphorylation.

Figure 27:
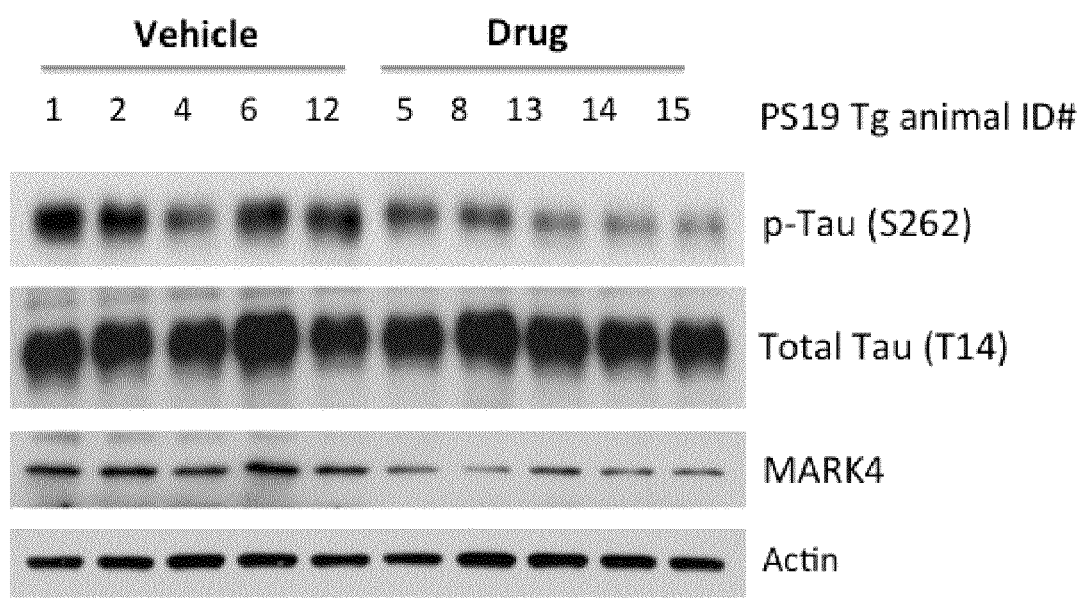
FIG. 27 shows western blot analysis of the effects of WP1130 treatment on MARK4 protein stability and on tau phosphorylation at the PAR-1/MARK target site (S262).

To test the effects of WP1130 in a mammalian model of AD, the drug was administered to Tauopathy mice (PS19) expressing the pathogenic P301S human tau transgene. Mice received intracerebroventricular (ICV) infusion of either WP1130 or vehicle controls and MARK4 and p-Tau levels were assessed by western blot. FIG. 27 shows that WP1130 significantly reduced levels of MAKR4 and phosphorylated tau relative to vehicle controls.

Figure 28:
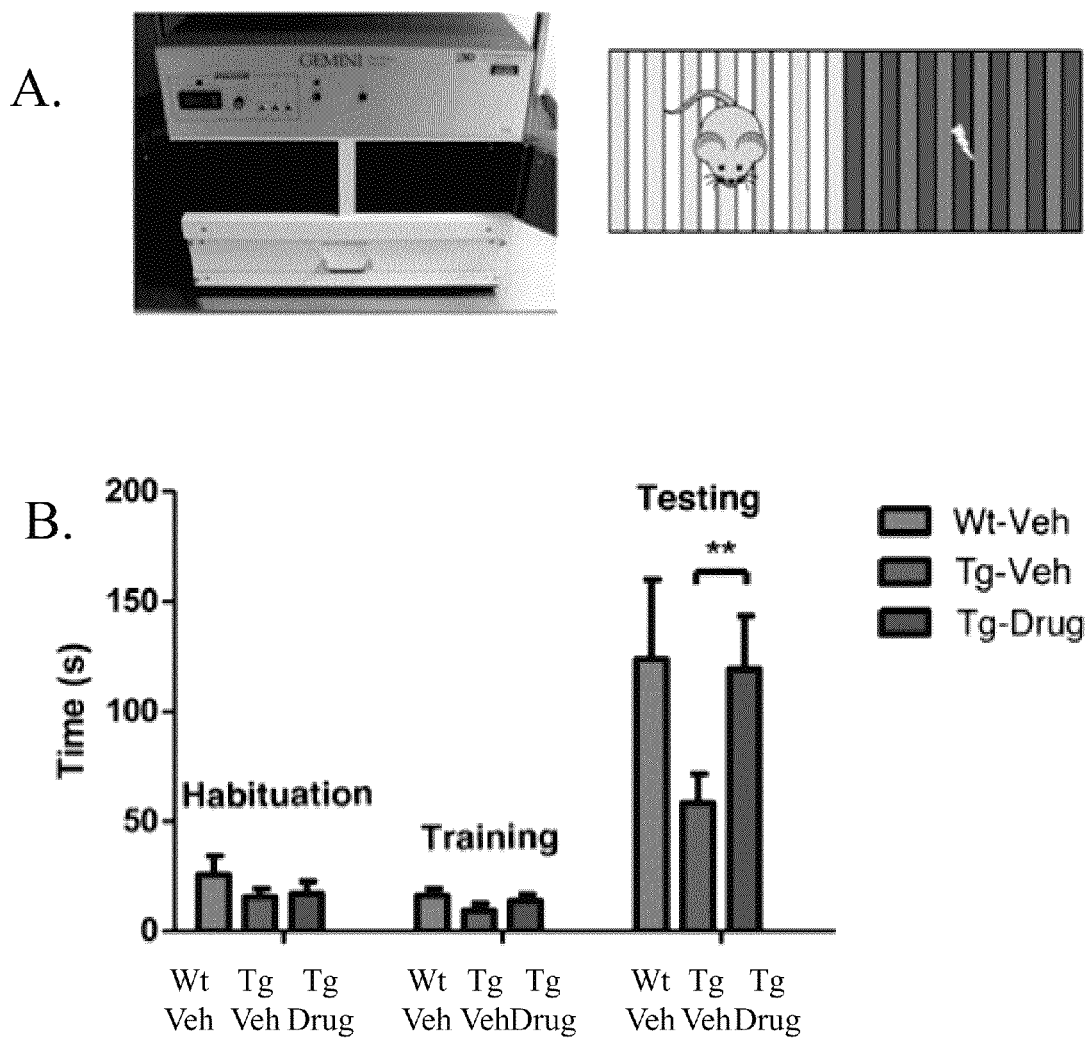
FIGS. 28A-B show results of a behavioral assay showing rescue of cognitive deficit of PS19 mice by WP1130 treatment.

The passive avoidance test was used to test whether WP1130 could rescue the learning and memory deficits expressed in the PS19 mice. During training, the animals were subjected to electric shock on the foot in the dark chamber. During testing, the trained animals were placed in the light chamber and the time it took the animals to enter the dark chamber (latency time) was recorded. FIG. 28 shows that WP1130-treated PS19 mice had latency times comparable to that of wt while vehicle treated PS19 mice remained significantly impaired.

Here a previously unknown mechanism of PAR-1 regulation in *Drosophila* that involves phosphorylation-dependent ubiquitination and degradation was revealed. This mechanism targets the phosphorylated and activated forms of PAR-1 for ubiquitination and degradation. Using the *Drosophila* NMJ synapses and the retina as assay systems, it was demonstrated that this newly identified mechanism of PAR-1 activity regulation is important for specifying synaptic morphology such as bouton number and for neuronal survival, and is highly relevant to AD pathogenesis. It is anticipated that this regulatory mechanism may also be relevant to PAR-1/MARK function in other physiological or developmental contexts.

These results show that active PAR-1 phosphorylated by LKB1 at the T408 site is normally present at a very low level. This could be due to a low basal phosphorylation of PAR-1 by LKB1, or that p-PAR-1 level is tightly regulated under physiological conditions. The further studies support that p-PAR-1 is normally tightly controlled by SCF(Slimb) for ubiquitination and degradation, and that FAF antagonizes SCF(Slimb) action in this process. This conclusion was supported by comprehensive genetic and biochemical interaction and studies. Although SCF(Slimb) and FAF are both likely to have more than one substrates in vivo, which might contribute to some of the phenotypes observed in the genetic interaction studies (FIG. 17), it is not clear how many targets are commonly regulated by them. The fact that PAR-1-RNAi could effectively rescue the synthetic effects between FAF and Slimb provided strong evidence that PAR-1 is a major mediator of their in vivo interaction. To our knowledge this is the first example of a common substrate regulated by SCF(Slimb) and FAF.

FIGS. 1a-1i show that FAF positively regulates PAR-1 activity and protein stability. FIGS. 1a-d show genetic interaction between PAR-1 and FAF in the fly retina. All flies were grown at 25° C. Images of female flies are shown. The genotypes are: GMR-Gal4/+control (FIG. 1a), GMR-Gal4>FAF[EP381] (FIG. 1b), GMR-Gal4>UAS-PAR 1 (FIG. 1c) and GMR-Gal4>UAS-PAR 1+FAF[EP381] (FIG. 1d) (n=16, 17, 16 and 16 animals, respectively). Statistically significant differences are P<0.001 (GMR-Gal4>UAS-PAR 1, GMR-Gal4>UAS-PAR 1+FAF[EP381]) as determined by Student's t-test. Experiments were performed in triplicate. Dashed lines outline the eye contour. Values represent areas of retinal surface normalized with GMR-Gal4/+control. Scale bar (FIGS. 1a-d), 100 μm. FIGS. 1e-h show representative NMJ terminals of the indicated genotypes revealed by anti-horseradish peroxidase (HRP) immunostaining. The genotypes are Mhc-Gal4/+control (figure e), Mhc-Gal4>FAF$^{EP352o}$ (FIG. 10, Mhc-Gal4>UAS-PAR 1 (FIG. 1g) and Mhc-Gal4>UAS-PAR-1+FAF$^{EP352o}$ (FIG. 1h). Scale bar (FIGS. 1e-h), 10 μm (1i) Quantification of the total number of boutons per muscle area on muscle 6/7 of A3 in the indicated genotypes. N indicates the number of animals analyzed. The error bars represent means±s.e.m. P-values were determined using two-tailed Student's t-test for each comparison. Experiments were performed in triplicate.

FIG. 1j shows western blot analysis of endogenous PAR-1protein level after FAF induction from hs-Myc-FAF. Actin serves as a loading control. Values represent PAR-1 levels normalized with wild-type control in three independent experiments. FIG. 1k shows western blot analysis showing in vivo ubiquitination of PAR-1 in animals co-expressing PAR-1-Myc and HA-Ub (lane 8). FIG. 1l shows in vitro deubiquitination assay using affinity-purified, HA-Ub-modified phsopho-PAR-1 as the substrate, and affinity-purified FAF as the enzyme. Note the decrease of poly-ubiquitinated PAR-1 and the corresponding increase of non-ubiquitinated or mono-ubiquitinated PAR-1 after FAF treatment. Brackets indicate ubiquitinated PAR-1 (Ub-PAR-1) in (k,l.). IB, immunoblot; n.s., not significant.

Figure 2:
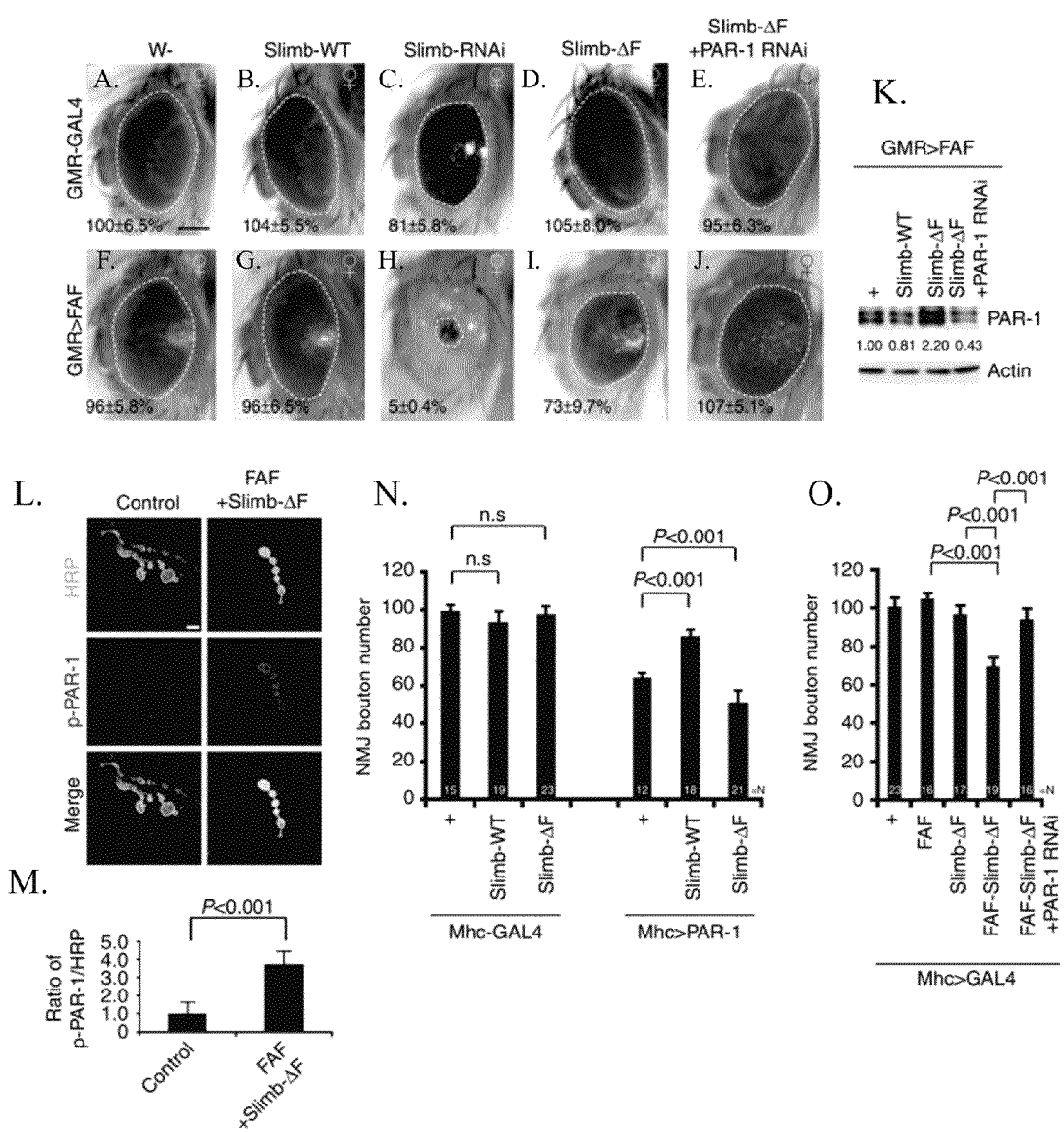

FIG. 2 shows that PAR-1 serves as a common substrate for FAF and Slimb.

FIGS. 2a-j show genetic interaction between FAF and Slimb in the retina. All flies were grown at 25° C. Images of female flies are shown. The genotypes are: GMR-Gal4/+ control (FIG. 2a), GMR-Gal4>UAS-Slimb-WT (FIG. 2b), GMR-Gal4>UAS-Slimb-RNAi (FIG. 2c), GMR-Gal4>UAS-Slimb-ΔF (FIG. 2d), GMR-Gal4>UAS-Slimb-ΔF+UAS-PAR-1-RNAi (FIG. 2e), GMR-Gal4>FAF$^{EP381}$ (FIG. 2f), GMR-Gal4>FAF$^{EP381}$+UAS-Slimb-WT (FIG. 2g), GMR-Gal4>FAF$^{EP381}$+UAS-Slimb-RNAi (FIG. 2h), GMR-Gal4>FAF$^{EP381}$+UAS-Slimb-ΔF (FIG. 2i) andGMR-Gal4>FAF$^{EP381}$+UAS-SlimbΔF+UAS-PAR-1-RNAi (FIG. 2j) (n=16, 17, 17, 18, 16, 17, 16, 18, 16 and 16 animals, respectively). Statistically significant differences are P<0.001 (GMR-Gal4/+control, GMR-Gal4>UAS-Slimb-RNAi; GMR-Gal4>FAF$^{EP381}$, GMR-Gal4>FAF$^{EP381}$+ UAS-Slimb-RNAi; GMR-Gal4>FAF$^{EP381}$, GMR-Gal4>FAF$^{EP381}$+UAS-Slimb-ΔF; GMR-Gal4>FAF$^{EP381}$+ UAS-Slimb-ΔF, GMR-Gal4>FAF$^{EP381}$+UAS-SlimbΔF+ UAS-PAR-1-RNAi) as determined by Student's t-test. Experiments were performed in triplicate. Dashed lines outline the eye contour. Values represent areas of retinal surface normalized with GMR-Gal4/+control. (FIGS. 2a-j) Scale bar, 100 μm. FIG. 2k shows western blot analysis of PAR-1 protein levels in the indicated genotypes. Actin serves as a loading control. Values represent PAR-1 levels in the indicated genotypes normalized with GMR-Gal4>FAF$^{EP381}$ control in three independent experiments. FIG. 2l shows double labeling of larval NMJs with anti-horseradish peroxidase (HRP) and anti-p-PAR-1. Merged images are shown in lower panels. The genotypes are: Mhc-Gal4>FAF+Slimb-ΔF and Mhc-Gal4/+control. Scale bar, 5 μm. FIG. 2m shows quantification of p-PAR-1 signals in FIG. 2l and FIG. 2m after normalization with HRP signal. FIG. 2N shows quantification of bouton numbers showing genetic interaction between PAR-1 and Slimb at the NMJ. N indicates the number of animals analyzed. The error bars represent means±s.e.m. P-values were determined using two-tailed Student's t-test for each comparison. Experiments were performed in triplicate. FIG. 2O shows quantification of bouton numbers showing genetic interactions among Slimb, FAF, and PAR-1 at the NMJ. N indicates the number of animals analysed. The error bars represent means±s.e.m. P-values were determined using two-tailed Student's t-test for each comparison. Experiments were performed in triplicate.

Figure 3:
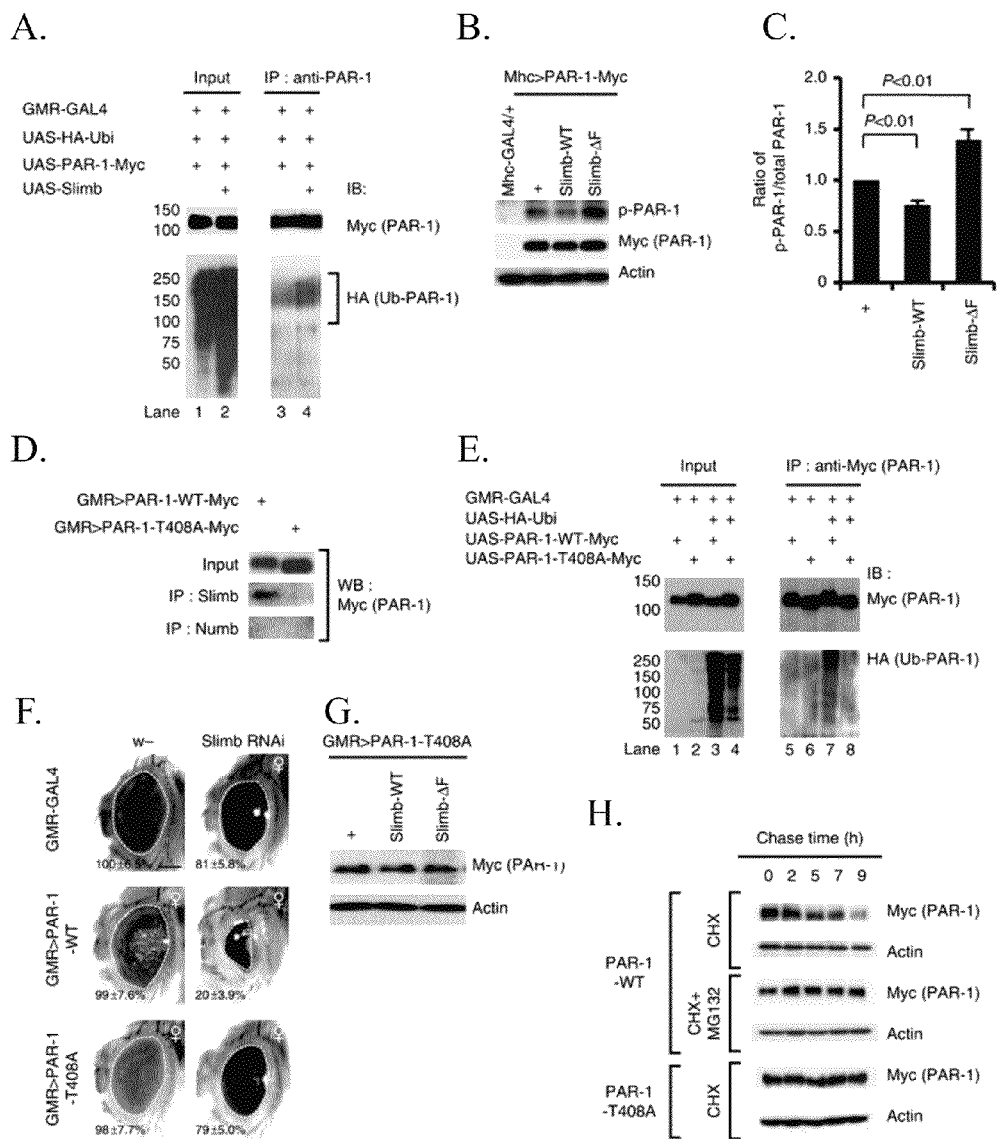
FIGS. 3A-H show that SCF Slimb-mediated ubiquitination of PAR-1 is coupled to its phosphorylation at T408.

FIG. 3 shows that SCF Slimb-mediated ubiquitination of PAR-1 is coupled to its phosphorylation at T408. FIG. 3a shows western blot analysis showing enhanced in vivo ubiquitination of PAR-1 by Slimb. FIG. 3b shows western blot analysis showing effects of Slimb-WT or Slimb-ΔF on transgene-derived total PAR-1 and p-PAR-1 levels. Actin serves as a loading control. FIG. 3c shows the quantification of the ratio of p-PAR-1/total PAR-1 levels shown in FIG. 3b. FIG. 3d shows an IP experiment showing selective binding of Slimb to PAR-1-WT compared with PAR-1-T408A. Anti-Numb IP serves as a negative control. FIG. 3e shows In vivo ubiquitination assay showing reduced ubiquitination of PAR-1-T408A compared with PAR-1-WT. FIG. 3f shows the genetic interaction between PAR-1 and Slimb in the retina in each of the indicated genotypes (GMR-Gal4/+control, n=16; GMR-Gal4>UAS-Slimb-RNAi, n=17; GMR-Gal4>UAS-PAR-1-WT, n=16; GMR-Gal4>UAS-PAR-1-WT+UAS-Slimb-RNAi, n=16; GMR-Gal4>UAS-PAR-1-T408A, n=17; and GMR-Gal4>UAS-PAR-1-T408A+UAS-Slimb-RNAi, n=17). Statistically significant differences are P<0.001 (GMR-Gal4>UAS-PAR-1-WT, GMR-Gal4>UAS-PAR-1-WT+UAS-Slimb-RNAi) as determined by Student's t-test. Experiments were performed in triplicate. Dashed lines outline the eye contour. Values represent areas of retinal surface normalized with GMR-Gal4/+control. Scale bar, 100 μm. FIG. 3g shows western blot analysis showing non-responsiveness of PAR-1-T408 protein abundance to Slimb activity. Actin serves as a loading control. (h) Pulse-chase assay showing differential stability of PAR-1-WT and PAR-1-T408A in HEK293 cells. Actin serves as a loading control. IB, immunoblot.

Figure 4:
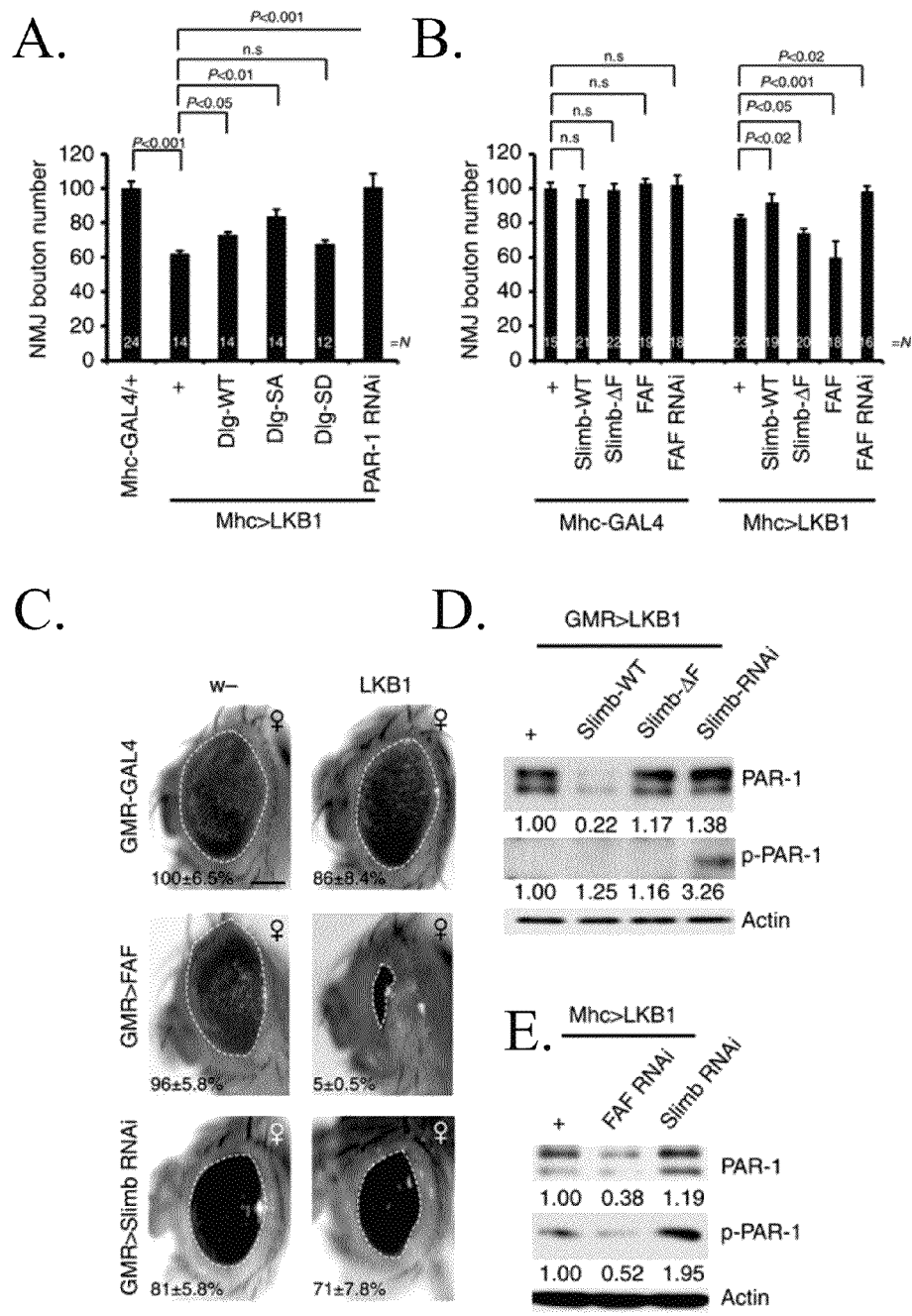
FIGS. 4A-E show that LKB1 cooperates with Slimb in the phosphorylation-dependent ubiquitination of PAR-1.

FIG. 4 shows that LKB1 cooperates with Slimb in the phosphorylation-dependent ubiquitination of PAR-1. FIG. 4a shows the quantification of NMJ boutons showing genetic interaction between LKB1 and PAR-1 or Dlg. N indicates the number of animals analysed. The error bars represent means±s.e.m. P-values were determined using two-tailed Student's t-test for each comparison. Experiments were performed in triplicate. FIG. 4b shows the quantification of NMJ bouton number showing genetic interaction between LKB1 and Slimb or FAF. N indicates the number of animals analysed. The error bars represent means±s.e.m. P-values were determined using two-tailed Student's t-test for each comparison. Experiments were performed in triplicate. (c) Genetic interaction between LKB and FAF or Slimb in the retina in each of the indicated genotypes (GMR-Ga/4/+control, n=16; GMR-Gal4>UAS-LKB1, n=16; GMR-Gal4>FAF$^{EP381}$, n=16; GMR-Gal4>FAF$^{EP381}$+UAS-LKB1, n=16; GMR-Gal4>UAS-Slimb-RNAi, n=17; GMR-Gal4>UAS-Slimb-RNAi+UAS-LKB1, n=17). Statistically significant differences are P<0.001 (GMR-Gal4>FAF$^{EP381}$ GMR-Gal4>FAF$^{EP381}$+UAS-LKB1) or P<0.03 (GMR-Gal4>UAS-Slimb-RNAi, GMR-Gal4>UAS-Slimb-RNAi+ UAS-LKB1) as determined by Student's t-test. Experiments were performed in triplicate. Dashed lines outline the eye contour. Values represent areas of retinal surface normalized with GMR-Gal4/+control. Scale bar, 100 μm. FIGS. 4d-e show western blot analyses showing the effects of LKB1 interaction with Slimb/FAF on PAR-1 and p-PAR-1 levels in adult fly head extracts (FIG. 4d) or third instar larvae body-wall muscle extracts (FIG. 4e). Values represent normalized PAR-1 and p-PAR-1 levels. Actin serves as loading control. n.s, not significant.

Figure 5:
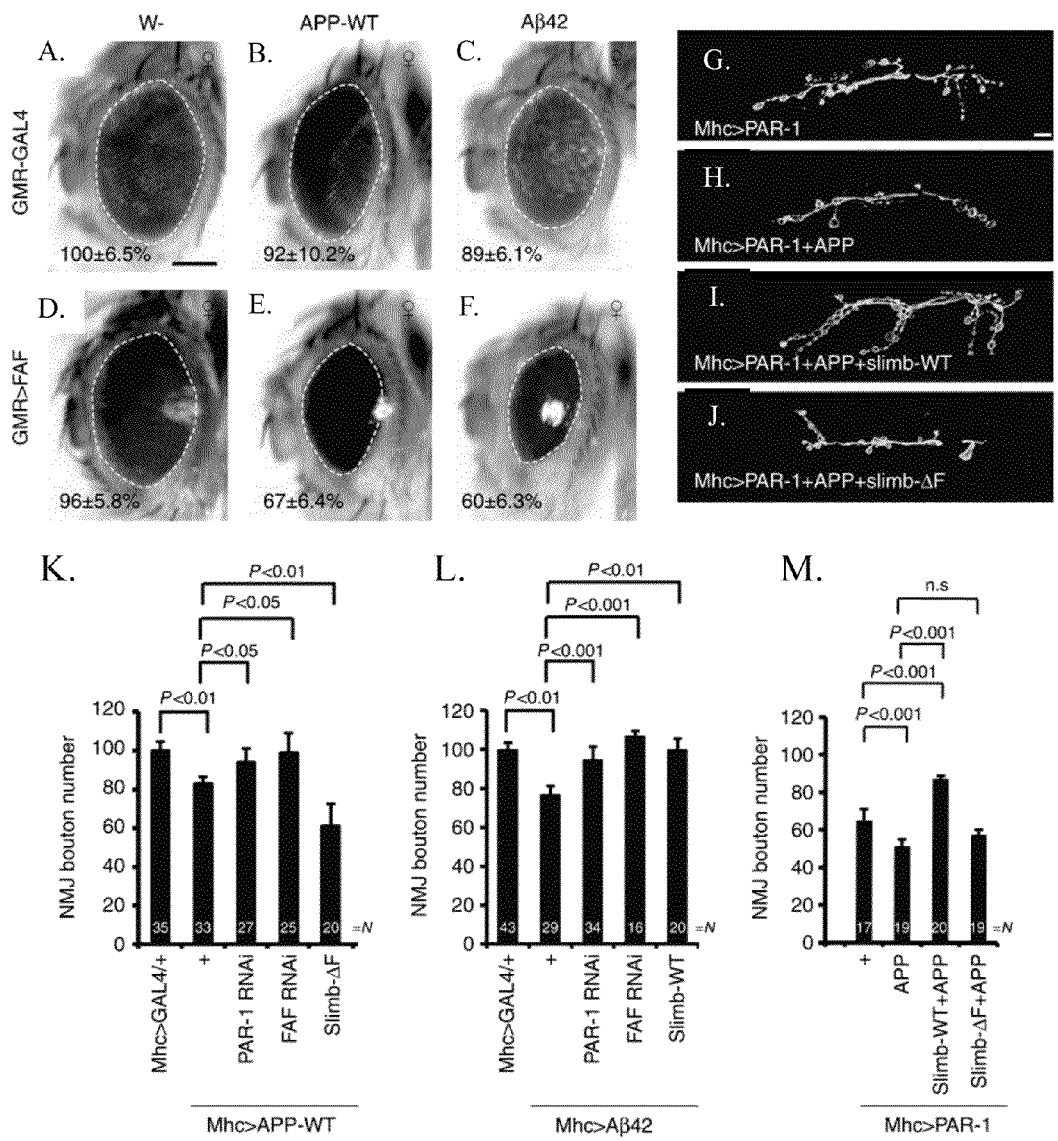
FIGS. 5A-M show that phosphorylation-dependent ubiquitination of PAR-1 mediates the toxicity of APP and Aβ-42.

FIG. 5 shows that phosphorylation-dependent ubiquitination of PAR-1 mediates the toxicity of APP and Aβ-42. FIGS. 5a-f show the genetic interaction between APP/Aβ-42 and FAF in the retina. Images of female flies are shown. All flies were grown at 25° C. The genotypes are: GMR-Gal4/+control (FIG. 5a), GMR-Gal4>UAS-APP-WT (FIG. 5b), GMR-Gal4>UAS-Aβ-42 (FIG. 5c), GMR-Gal4>FAF$^{EP381}$ (FIG. 5d), GMR-Gal4>FAF$^{EP381}$+UAS-APP-WT (FIG. 5e) and GMR-Gal4>FAF$^{EP381}$+UAS-Aβ-42 (FIG. 5f) (n=16, 18, 16, 17, 16 and 16 animals, respectively). Statistically significant differences are P<0.01 (GMR-Gal4/+control, GMR-Gal4>UAS-Aβ-42) or P<0.001 (GMR-Gal4>FAF$^{EP381}$, GMR-Gal4>FAF$^{EP381}$+UAS-APP-WT; GMR-Gal4>FAF$^{EP381}$, GMR-Gal4>FAF$^{EP381}$+UAS-Aβ-42) as determined by Student's t-test. Experiments were performed in triplicate. Dashed lines outline the eye contour. Values represent areas of retinal surface normalized with GMR-Gal4/+control. Scale bar (FIGS. 5a-f), 100 µm. (FIGS. 5g-j) Representative anti-horseradish peroxidase immunostaining showing larval NMJ morphology of the following genotypes: Mhc-Gal4>UAS-PAR-1 (FIG. 5g), Mhc-Gal4>UAS-PAR-1+UAS-APP-WT (FIG. 5h), Mhc-Gal4>UAS-PAR-1+UAS-APP-WT UAS-Slimb-WT (i) and Mhc-Gal4>UAS-PAR-1+UAS-APP-WT+UAS-Slimb-ΔF (FIG. 5j). Scale bar, 10 µm. FIGS. 5k-m show the quantification of NMJ bouton numbers showing genetic interactions among APP, PAR-1, Slimb and FAF (FIG. 5k), among Aβ-42, PAR-1, Slimb and FAF (FIG. 5l), or between APP+PAR-1 and Slimb (FIG. 5m). Flies were grown at 29° C. (FIG. 5k) or 25° C. (FIGS. 5l,m). N indicates the number of animals analysed. The error bars represent means±s.e.m. P-values were determined using two-tailed Student's t-test for each comparison. Experiments were performed in triplicate. n.s, not significant.

Figure 6:
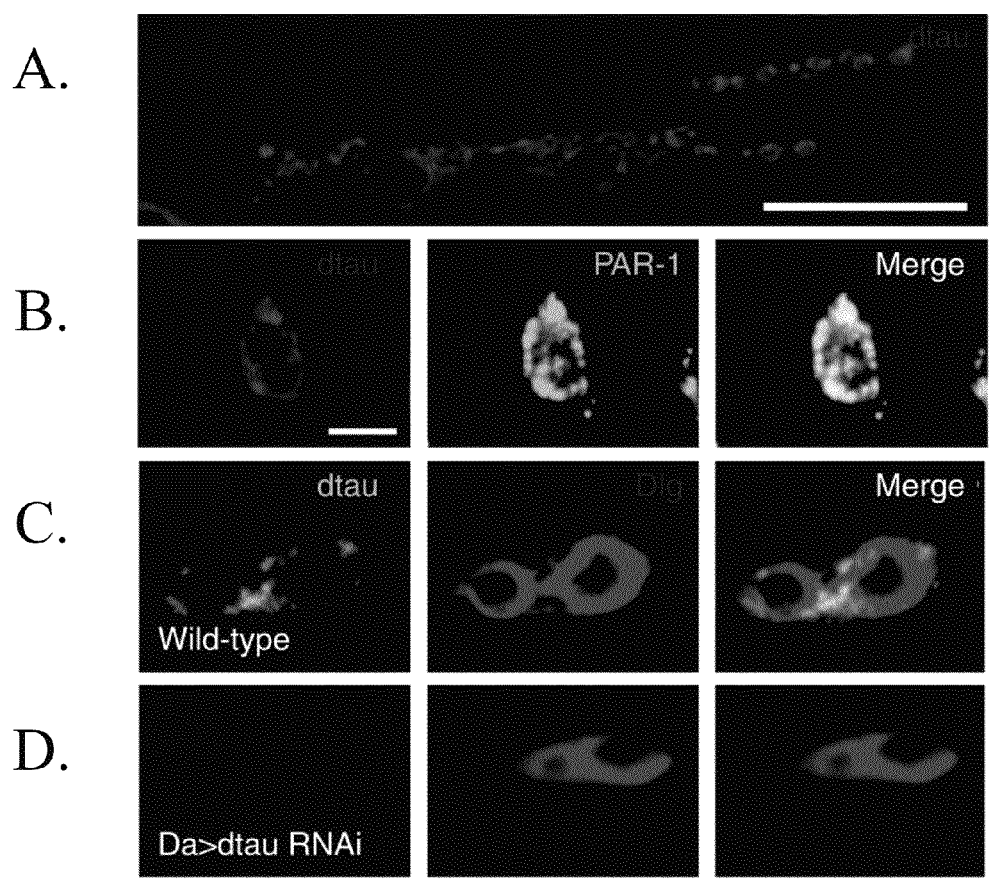
FIGS. 6A-F show that phospho-dtau mediates the postsynaptic toxicity of PAR-1.
Figure 6:
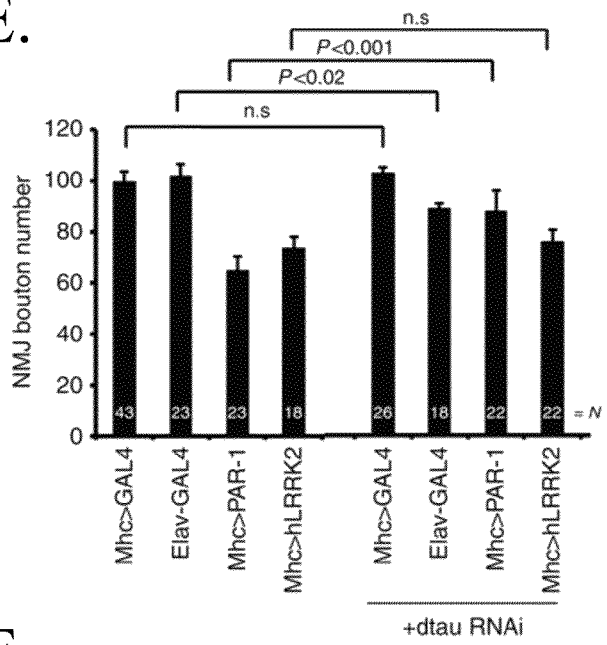
Figure 6:
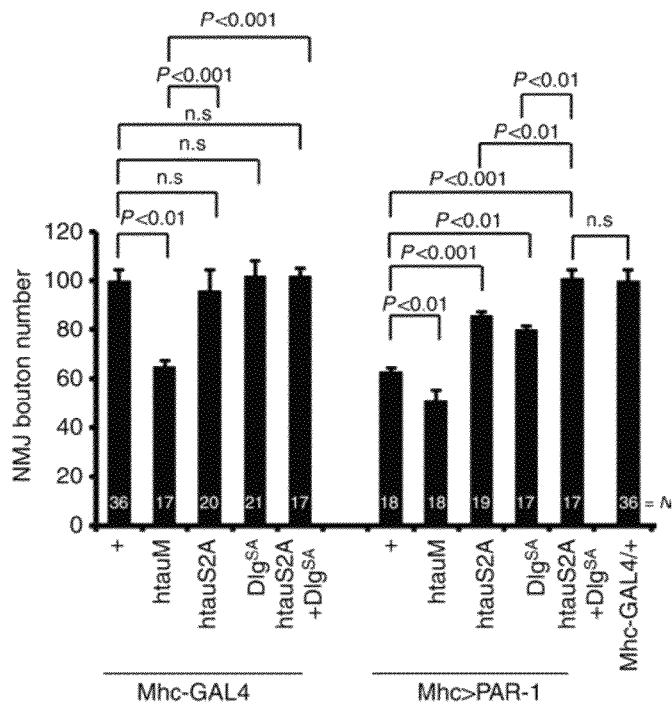

FIG. 6 shows that phospho-dtau mediates the postsynaptic toxicity of PAR-1. FIGS. 6a-d show immunostaining showing dtau localization at third instar larval muscle and NMJ. FIG. 6a shows WT larvae stained with anti-dtau antibody shown in red. Scale bar, 50 µm. FIGS. 6b-d show higher magnification images of NMJ boutons double-labelled with anti-dtau and anti-PAR-1 in WT animals FIG. 6b, or labelled with anti-dtau and anti-Dlg in WT FIG. 6c and Da-Gal4>dtau-RNAi animals FIG. 6d. Scale bar, 5 µm. FIG. 6e shows the quantification of NMJ bouton number showing specific genetic interaction between PAR-1 and dtau, but not between hLRRK2 and dtau. N indicates the number of animals analysed. The error bars represent means±s.e.m. P-values were determined using two-tailed Student's t-test for each comparison. Experiments were performed in triplicate. FIG. 6f shows the quantification of NMJ boutons showing mediation of the postsynaptic effects of PAR-1 by both Dlg and tau. N indicates the number of animals analysed. The error bars represent means±s.e.m. P-values were determined using two-tailed Student's t-test for each comparison. Experiments were performed in triplicate. n.s, not significant.

Figure 7:
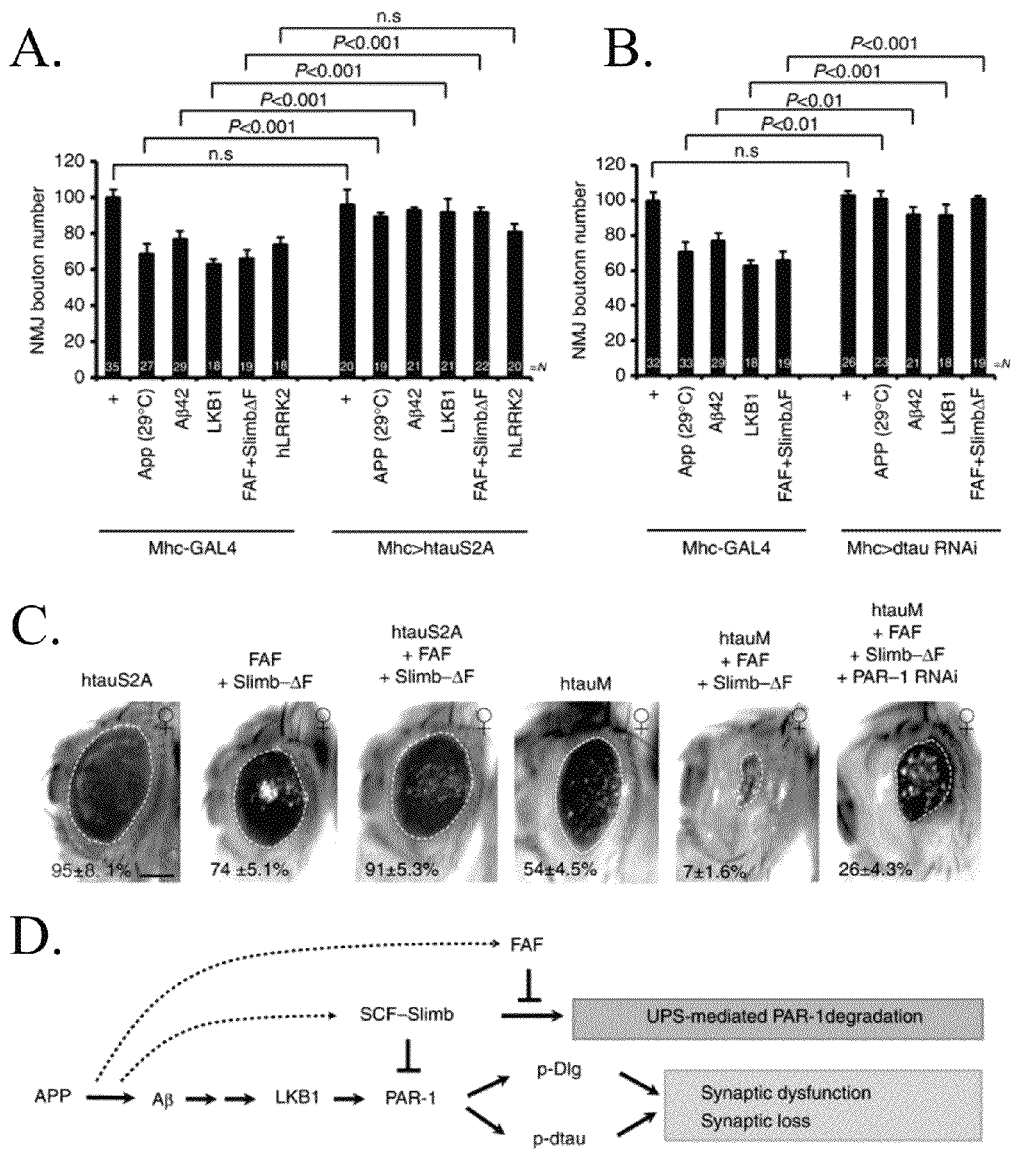
FIGS. 7A-D show that the dtau mediates the toxic effects of APP/Aβ-42 and the direct modifiers of PAR-1.

FIG. 7 shows that the dtau mediates the toxic effects of APP/Aβ-42 and the direct modifiers of PAR-1. FIGS. 7a-b show the quantification of NMJ bouton number showing rescue by htauS2A (FIG. 7a) or dtau-RNAi (FIG. 7b) of the bouton-loss phenotypes induced by manipulations of the expression APP/A β-42 or the PAR-1 ubiquitination modifiers. N indicates the number of animals analyzed. The error bars represent means±s.e.m. P-values were determined using two-tailed Student's t-test for each comparison. Experiments were performed in triplicate. FIG. 7c shows genetic interaction between tau and the modifiers of PAR-1 in the retina. Eye images of female flies are shown. All flies were grown at 22° C. The genotypes are: GMR-Gal4>UAS-htauS2A (n=16), GMR-Gal4>FAF$^{EP381}$+UAS-Slimb-ΔF (n=16), GMR-Gal4>UAS-htauS2A+FAF$^{EP381}$+UAS-Slimb-ΔF (n=17), GMR-Gal4>UAS-htauM (n=17), GMR-Gal4>UAS-htauM+FAF$^{EP381}$+UAS-Slimb-ΔF (n=18) and GMR-Gal4>UAS-htauM+FAF$^{EP381}$+UAS-Slimb-ΔF+UAS-PAR 1-RNAi (n=18). Statistically significant differences are P<0.001 (GMR-Gal4>FAF$^{EP381}$+UAS-Slimb-ΔF, GMR-Gal4>htauS2A+FAF$^{EP381}$+UAS-Slimb-ΔF; GMR-Gal4>UAS-htauM, GMR-Gal4>UAS-htauM+FAF$^{EP381}$+UAS-Slimb-ΔF; GMR-Gal4>UAS-htauM+FAF$^{EP381}$+UAS-Slimb-ΔF, GMR-Gal4>UAS-htauM+FAF$^{EP381}$+UAS-Slimb-ΔF+UAS-PAR-1-RNAi) as determined by Student's t-test. Experiments were performed in triplicate. Dashed lines outline the eye contour. Values represent areas of retinal surface normalized with GMR-Gal4/+control. Scale bar, 100 µm. FIG. 7d shows a model depicting the possible signaling pathways linking APP/Aβ-42 to synaptic dysfunction and synapse loss seen in AD. Dashed lines indicate potential direct regulations. n.s, not significant; UPS, Ubiquitin-proteasome system.

Figure 8:
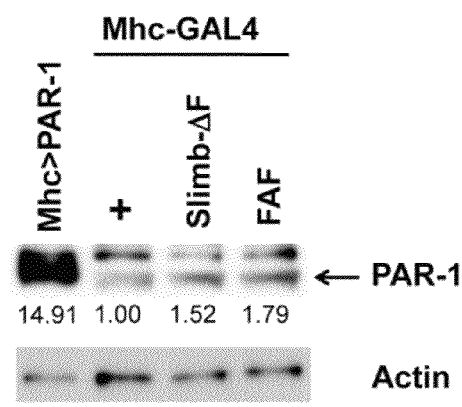
FIGS. 8A-B show western blot analysis of PAR-1 and p-PAR-1 levels in various genotypes.
Figure 8:
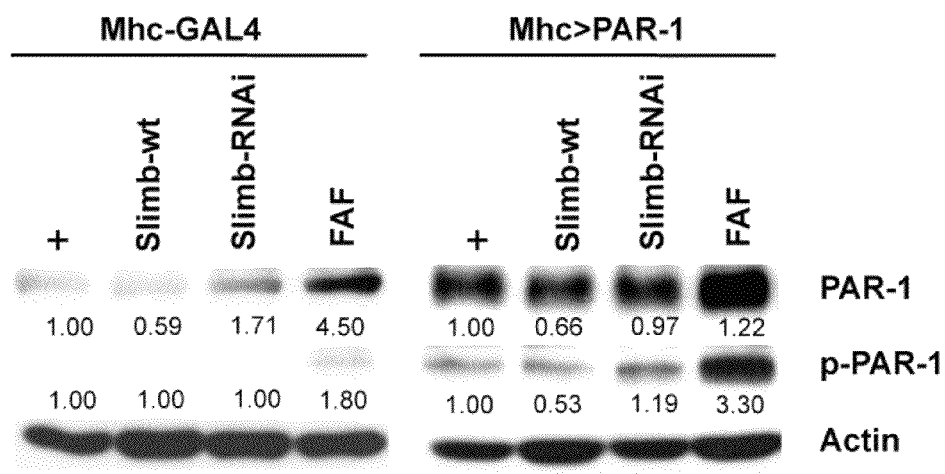

FIG. 8. Western blot analysis of PAR-1 and p-PAR-1 levels in various genotypes. (a) Western blot analysis comparing levels of endogenous PAR-1 after Slimb or FAF manipulation using the muscle-specific Mhc-Gal4 driver that did not affect NMJ bouton number, with the level of transgenic PAR-1 in Mhc-Gal4>PAR-1animals that showed reduced bouton number. (b) Western blot analysis of endogenous PAR-1 and p-PAR-1 protein levels or transgenic PAR-1 and p-PAR-1 levels after Slimb or FAF manipulation. Mhc-Gal4 was used to direct transgene expression. Actin serves as a loading control. Values represent normalized PAR-1 or p-PAR-1 levels from three independent experiments.

Figure 9:
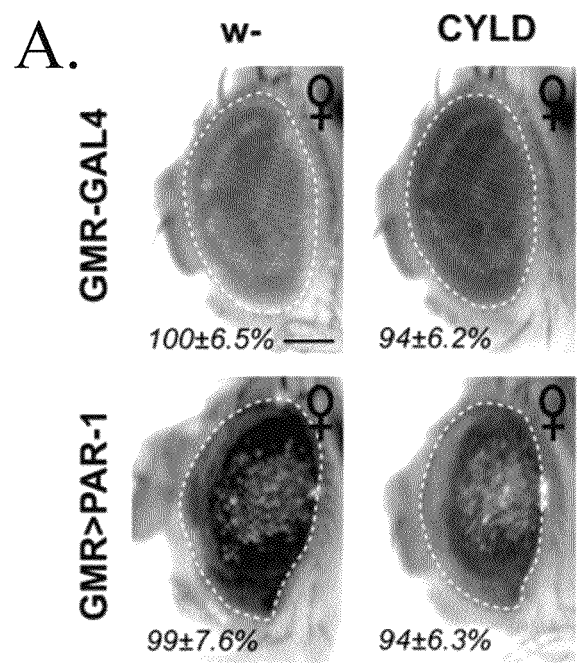
FIGS. 9A-B show genetic interaction tests between PAR-1 and CYLD in the fly eye and NMJ.
Figure 9:
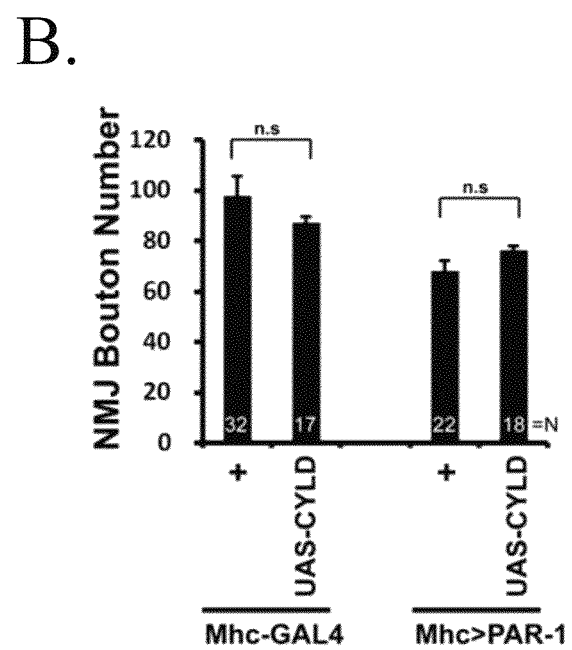

FIG. 9 shows genetic interaction tests between PAR-1 and CYLD in the fly eye and NMJ. (a) Testing for genetic interaction between PAR-1 and CYLD in the fly eye. All flies were raised at 25° C. Images of female flies are shown. CYLD failed to modify PAR-1 induced rough eye phenotype. The genotypes are: GMR-Gal4/+(n=16), GMR-Gal4>UAS-CYLD (n=16), GMR-Gal4>UAS-PAR 1 (n=17) and GMR-Gal4>UASPAR-1+UAS-CYLD (n=17). Experiments were performed in triplicate. Dashed lines outline the eye contour. Values represent areas of retinal surface normalized with GMRGal4/+control. Scale bar: 100 µm. (b) Testing for genetic interaction between PAR-1 and CYLD in the NMJ. The bar graph shows quantification of bouton numbers in the indicated genotypes. Postsynaptic co-expression of CYLD did not affect the bouton loss phenotype caused by PAR-1 overexpression. N indicates the number of animals analyzed. The error bars represent means±SEM. P-values were determined using two-tailed Student's t-test for each comparison. Experiments were performed in triplicate.

Figure 10:
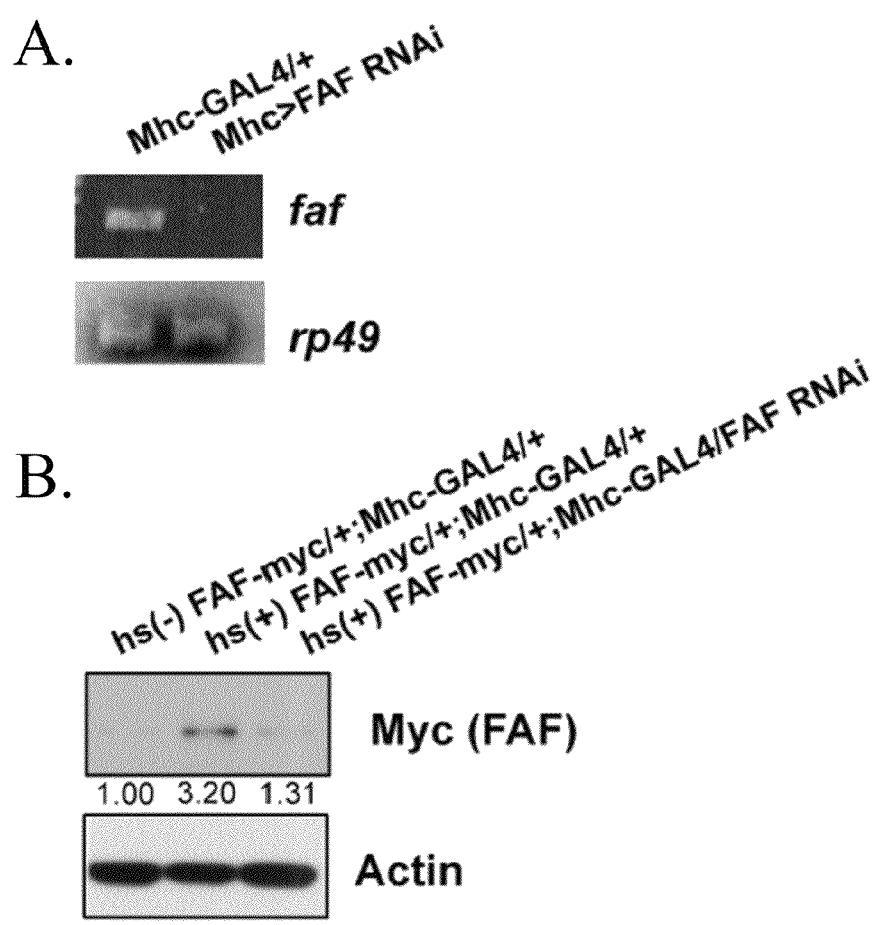
FIGS. 10A-B show the validating of the efficiency of the FAF RNAi transgene used in this study.
Figure 11:
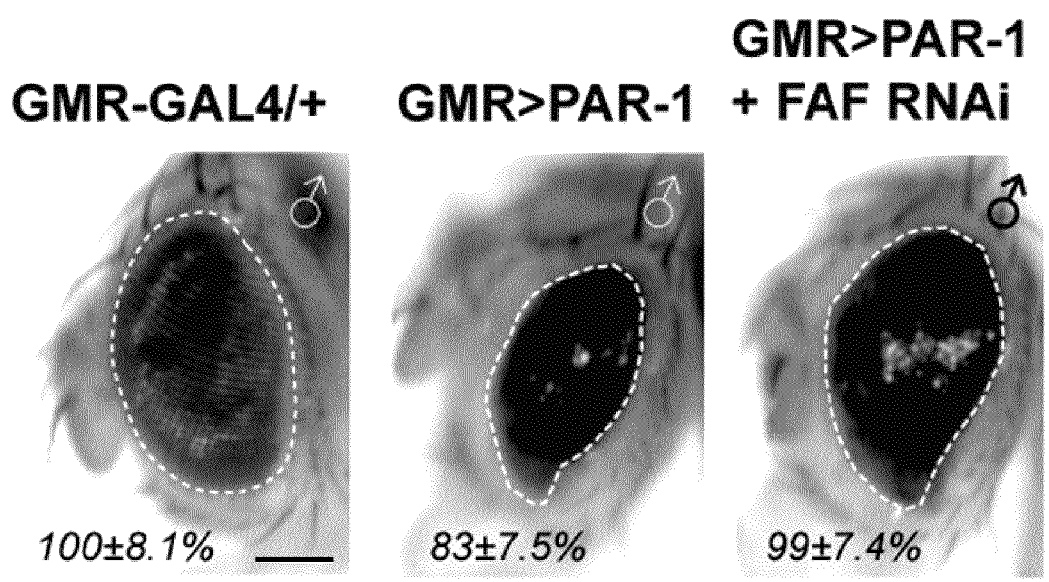
FIG. 11 shows the genetic interaction between PAR-1 and FAF in the fly eye.

FIG. 10 shows the validating of the efficiency of the FAF RNAi transgene used in this study. (a) RT-PCR analysis of FAF mRNA levels in wild-type and MhcGal4>FAF RNAi larvae. Total RNAs prepared from third instar larval body wall muscle were used. Rp49 serves as a loading control. (b) Western blot analysis showing that the FAF RNAi transgene efficiently knocked down the expression of FAF-Myc protein expressed from an hs-FAF-Myc transgene. Thoracic extracts prepared from heat-shocked adult animals were used. Actin serves as a loading control. Values represent averaged FAF-Myc levels normalized with non heat-shock control, which shows basal leaky expression of the transgene, from three independent experiments.

FIG. 11 shows the genetic interaction between PAR-1 and FAF in the fly eye. The reduced eye size caused by PAR-1 overexpression was rescued by FAFRNAi. Eye images of male flies of the indicated genotypes are shown. The genotypes are: GMR-Gal4/+(n=16), GMR-Gal4>UAS-PAR-1 (n=18) and GMR-Gal4>UAS-PAR-1+UASFAF RNAi (n=17). Experiments were performed in triplicate. Dashed lines outline the eye contour. Values represent areas of retinal surface normalized with GMR-Gal4/+control. Scale bar: 100 µm FIG. 12 is a western blot analysis showing that a control deubiquitinating enzyme CYLD did not significantly affect PAR-1 protein level. Actin serves as a loading control. Values represent PAR-1 levels normalized by actin levels from three independent experiments.

FIG. 13 shows that ubiquitinated forms of PAR-1 and p-PAR-1 accumulate in faf mutant. (a) Western blot analysis showing moderate increase of ubiquitinated forms of PAR-1 in $faf^{FO8}/faf^{BX4}$ mutant thorax extracts. Actin serves as a loading control. (b) Western blot analysis showing a dramatic increase of ubiquitination p-PAR-1 immunoprecipitated from $faf^{FO8}/faf^{BX4}$ mutant fly head extracts. Brackets indicate ubiquitinated PAR-1 (Ub-PAR-1).

FIG. 14 shows the effects of inhibition of Slimb by RNAi on NMJ bouton number. (a) Quantification of data showing the effect of postsynaptic Slimb RNAi on the total number of boutons per muscle area on muscle 6/7 of A3. Significant difference in NMJ bouton number was observed in Mhc-Gal4>UAS-Slimb RNAi animals compared to Mhc-Gal4/+ control. N indicates the number of animals analyzed. N indicates the number of animals analyzed. The error bars represent means±SEM. P-values were determined using two-tailed Student's t-test for each comparison. Experiments were performed in triplicate. (b) Representative immunostaining with anti-HRP showing NMJ morphology in the indicated genotypes. (c) Western blot analysis of endogenous PAR-1, p-PAR-1 and Slimb levels in GMR>Slimb RNAi animals. The Slimb RNAi transgene is effective in knocking down Slimb protein expression. Actin serves as a loading control.

Figure 15:
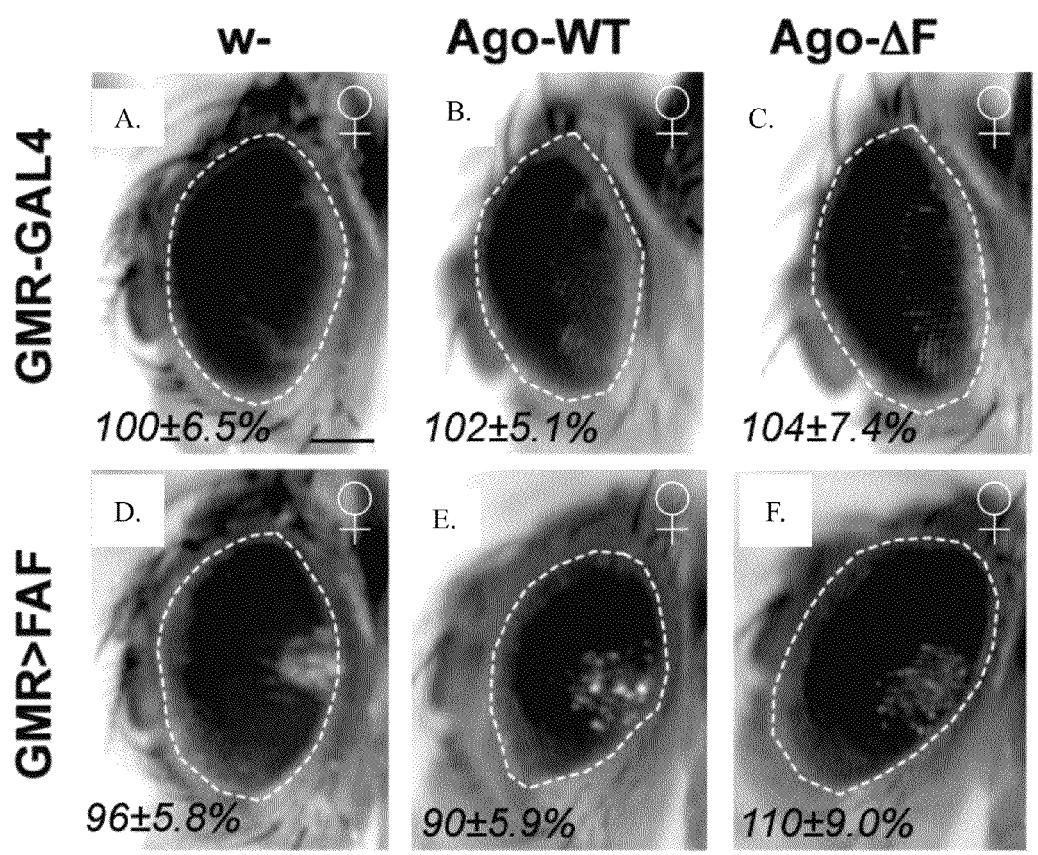
FIGS. 15A-F show testing for genetic interaction between FAF and Ago in the fly Eye. Eye images of female flies of the indicated genotypes are shown. GMR-Gal4/+(FIG. 15A), GMR-Gal4>UAS-Ago-WT (FIG. 15B), GMR-Gal4>UAS-Ago-ΔF (FIG. 15C), GMR-Gal4>FAF$^{EP381}$ (FIG. 15D), GMR-Gal4>FAF$^{EP381}$+UAS-Ago-WT (FIG. 15E), and GMR-Gal4>FAF$^{EP381}$+UAS-Ago-ΔF (FIG. 15F).
Figure 16:
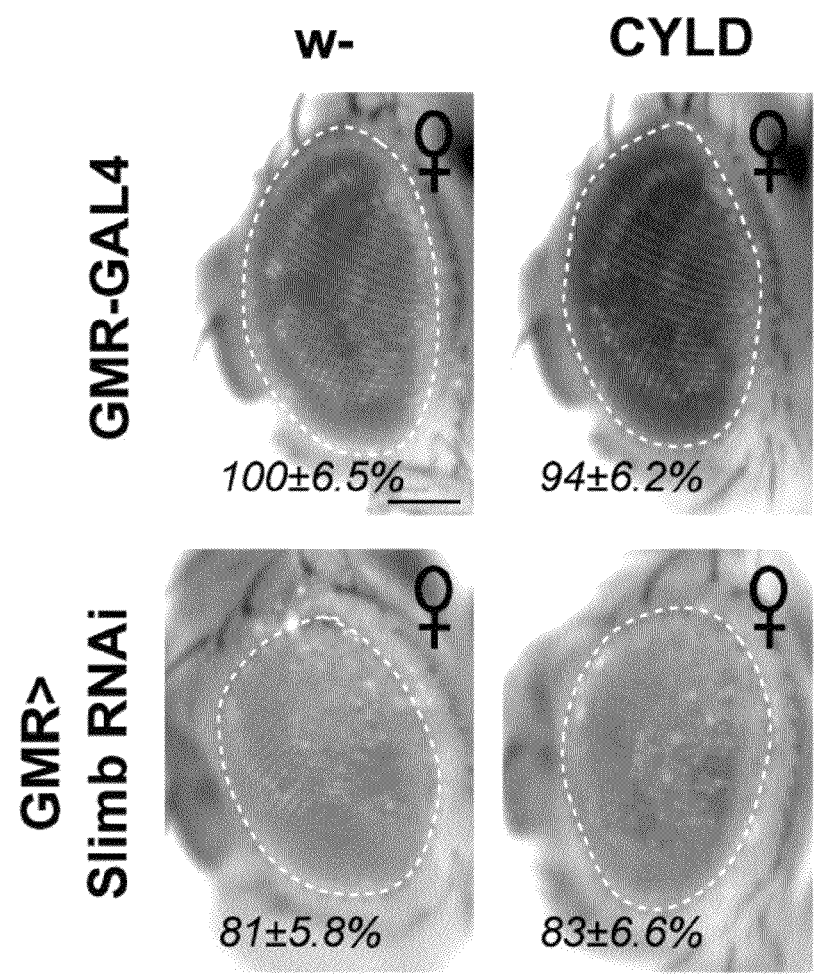
FIG. 16 shows testing for genetic interaction between Slimb and CYLD in the fly eye.

FIG. 15 shows testing for genetic interaction between FAF and Ago in the fly Eye. Eye images of female flies of the indicated genotypes are shown. All flies were grown at 25° C. There is no significant change of eye size or morphology in wild type or FAF(EP381) overexpression background with or without Ago transgene expression. The genotypes are: GMR-Gal4/+(a), GMR-Gal4>UAS-Ago-WT (b), GMR-Gal4>UAS-Ago-ΔF (c), GMR-Gal4>FAF$^{EP381}$ (d), GMR-Gal4>FAF$^{EP381}$+UAS-Ago-WT (e), and GMR-Gal4>FAF$^{EP381}$+UAS-Ago-ΔF (f) (n=16, 18, 17, 19, 16 and 16 animals, respectively). Experiments were performed in triplicate. Dashed lines outline the eye contour. Values represent areas of retinal surface normalized with GMR-Gal4/+ control. Scale bar: 100 µm.

FIG. 16 shows testing for genetic interaction between Slimb and CYLD in the fly eye. The genotypes are: GMR-Gal4/+(n=16), GMR-Gal4>UAS-CYLD (n=16), GMR-Gal4>UAS-Slimb RNAi (n=18) and GMR-Gal4>UAS-Slimb RNAi+UAS-CYLD (n=17). All flies were raised at 25° C. Images of female flies are shown. No significant difference in eye size between GMR>Slimb RNAi and GMR>Slimb RNAi+CYLD was found. This result demonstrates that the genetic interaction between Slimb and FAF is specific. Experiments were performed in triplicate. Dashed lines outline the eye contour. Values represent areas of retinal surface normalized with GMR-Gal4/+control. Scale bar: 100 µm.

Figure 17:
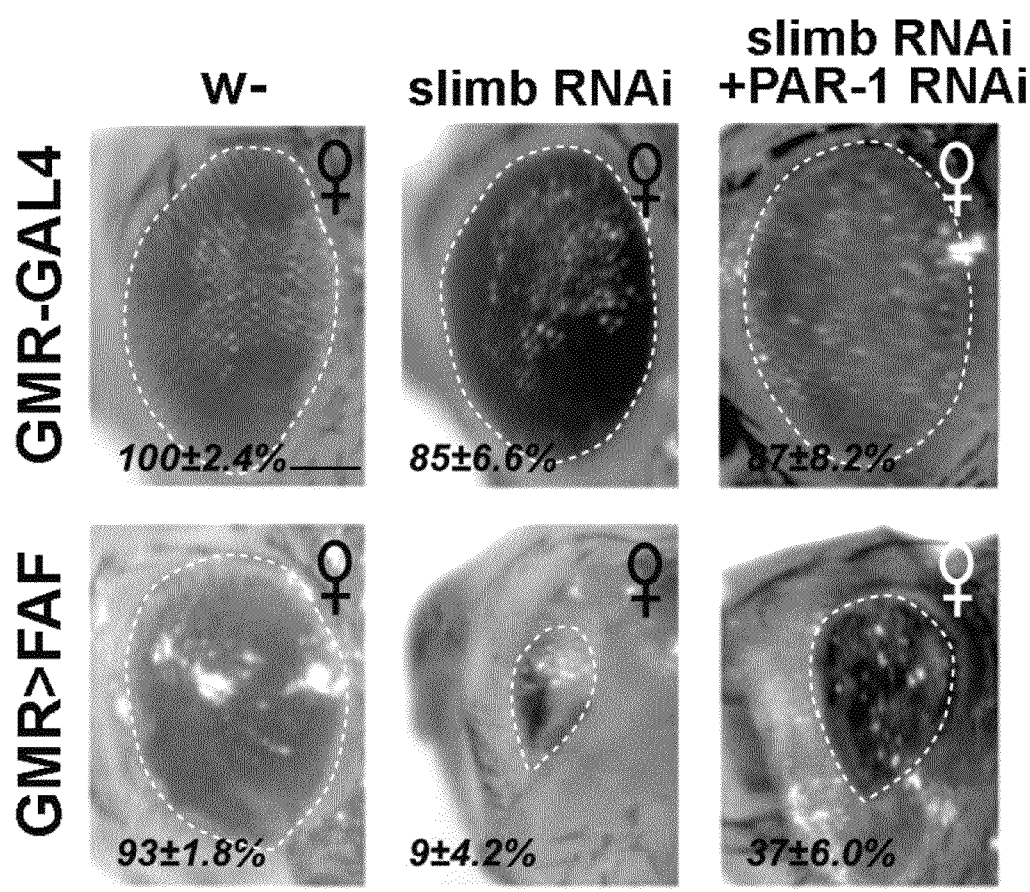
FIG. 17 shows mediation of the genetic interaction between Slimb and FAF by PAR-1.

FIG. 17 shows mediation of the genetic interaction between Slimb and FAF by PAR-1. The genotypes are: GMR-Gal4/+(n=10), GMR-Gal4>UAS-Slimb RNAi (n=11), GMR-Gal4>UAS-Slimb RNAi+PAR-1 RNAi (n=10), GMR-Gal4>FAF$^{EP381}$ (n=10), GMR-Gal4>FAF$^{EP381}$+UAS-Slimb RNAi (n=9) and GMR-Gal4>FAF$^{EP381}$+UAS-Slimb RNAi+PAR-1 RNAi (n=10). Statistically significant differences are P<0.001 (GMR-Gal4/+, GMR-Gal4>UAS-Slimb RNAi; GMR-Gal4>FAF$^{EP381}$, GMR-Gal4>FAF$^{EP381}$+UAS-Slimb RNAi; GMR-Gal4>FAF$^{EP381}$+UAS-Slimb RNAi, GMR-Gal4>FAF$^{EP381}$+UAS Slimb RNAi+UAS-PAR-1 RNAi) as determined by Student's t-test. Experiments were performed in triplicate. All flies were raised at 22° C. Because the co-expression of FAF and Slimb RNAi caused pupae lethality, images of pharate adult female flies dissected out of pupal cases are shown. The significant rescue of FAF and Slimb RNAi co-expression induced small eye phenotype by PAR-1 RNAi supports that the genetic interaction between Slimb and FAF is partially mediated by PAR-1. Other substrates likely contributes to the eye phenotype as well. Experiments were performed in triplicate. Dashed lines outline the eye contour. Values represent areas of retinal surface normalized with GMR-Gal4/+control. Scale bar: 100 µm.

Figure 18:
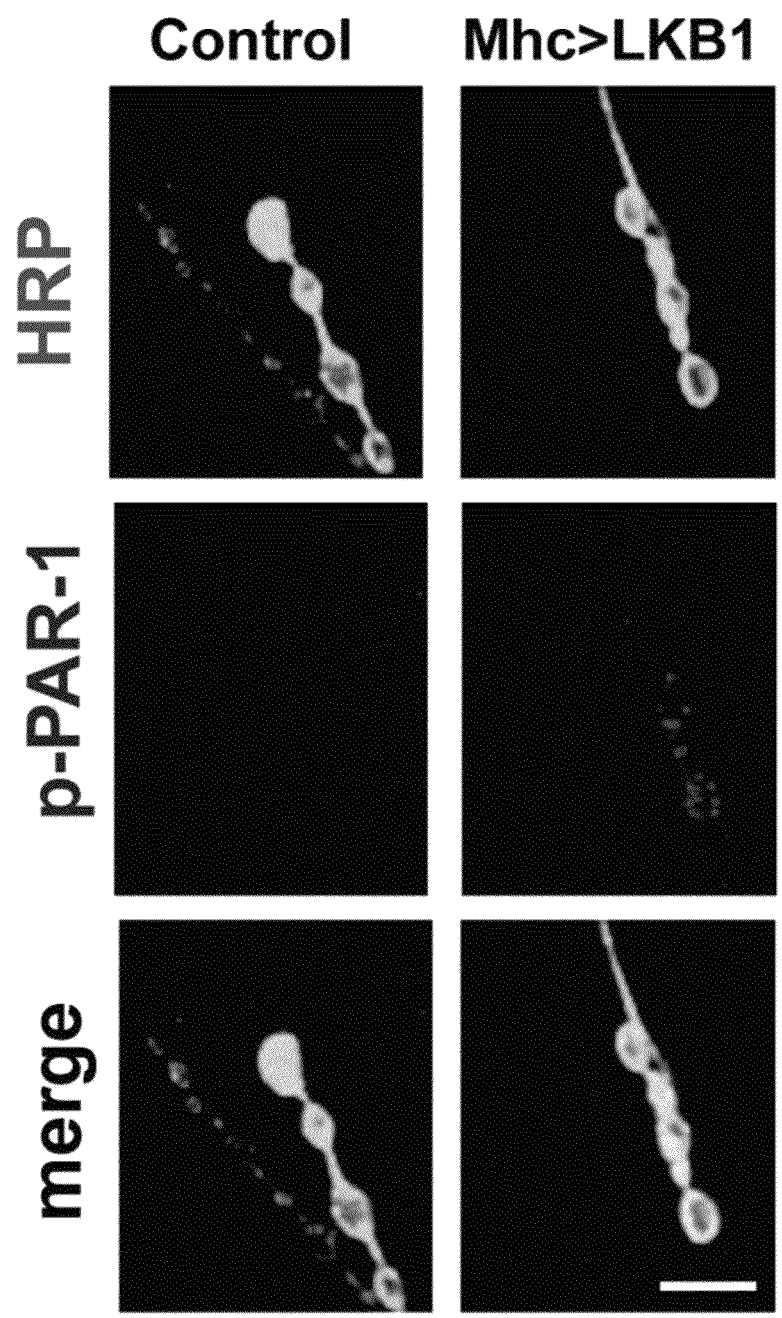
FIG. 18 shows a control experiment demonstrating the specificity of the phospho-PAR-1 signal detected in larval NMJ.

FIG. 18 shows a control experiment demonstrating the specificity of the phospho-PAR-1 signal detected in larval NMJ. Images show double labeling of larval NMJs with anti-HRP and anti-p-PAR-1. p-PAR-1 signal is increased in LKB1 overexpression animals. Scale bars: 10 µm.

FIG. 19 shows that slimb expression is more enriched at the postsynaptic compartment. (a) Double-label experiment showing that phospho-PAR-1 precisely co-localized with Slimb at the larval NMJ. (b) Double-labeling with anti-HRP and anti-Slimb showing the effects of pre-(elav-Gal4 driven) or post-synaptic (Mhc-Gal4 driven) RNAi knockdown of Slimb on synaptic Slimb signals. Scale bars: a and b, 5 µm.

Figure 20:
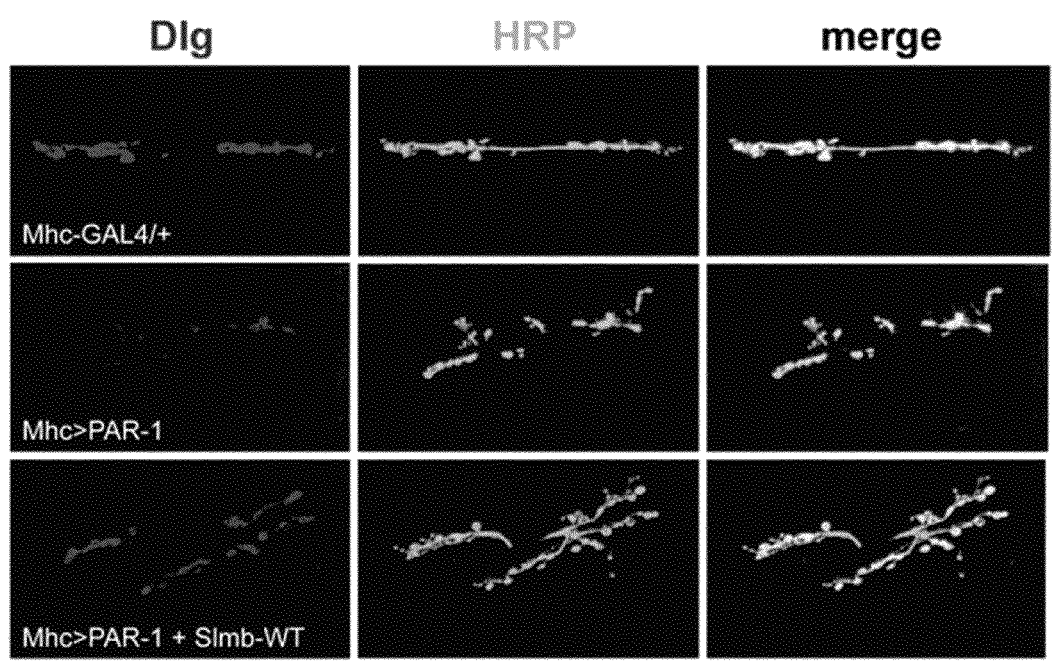
FIG. 20 shows rescue of PAR-1 overexpression induced Dlg mislocalization by Slimb. Co-expression of Slimb-WT largely rescued the Dlg delocalization phenotype caused by PAR-1 overexpression. Double-labeling of larval NMJs of the indicated genotypes with anti-Dlg, anti-HRP, and merged images are shown.

FIG. 20 shows rescue of PAR-1 overexpression induced Dlg mislocalization by Slimb. Co-expression of Slimb-WT largely rescued the Dlg delocalization phenotype caused by PAR-1 overexpression. Double-labeling of larval NMJs of the indicated genotypes with anti-Dlg, anti-HRP, and merged images are shown.

Figure 21:
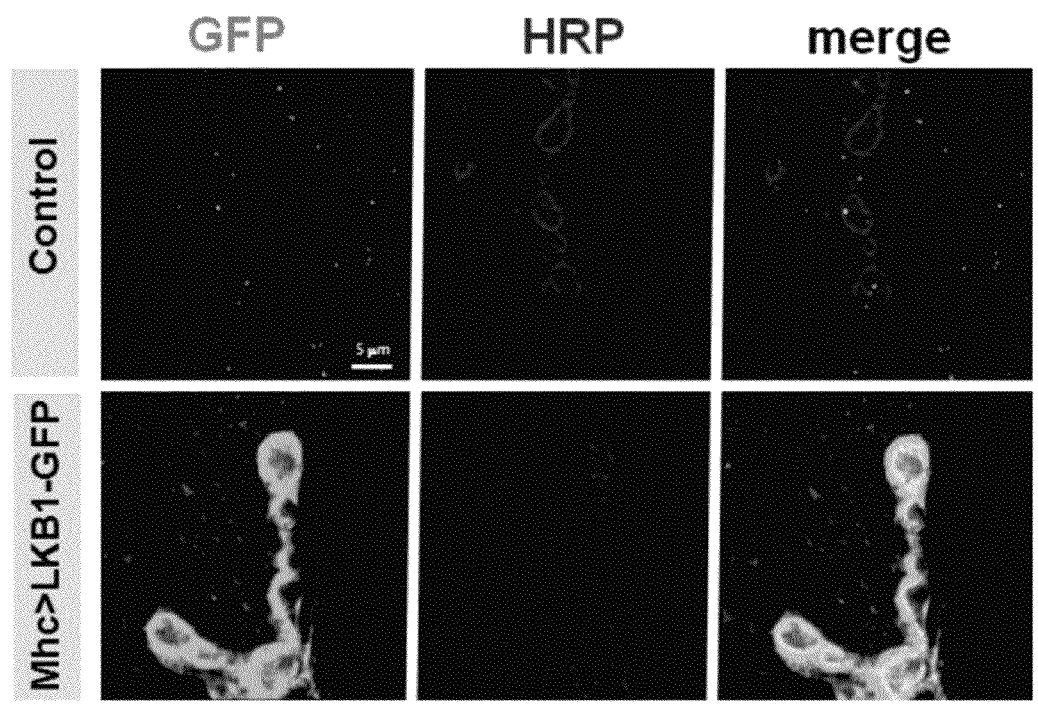
FIG. 21 shows localization of LKB1-GFP at the larval NMJ. Double-labeling with anti-HRP and anti-GFP of wild-type, elav-Gal4>LKB1-GFP, or Mhc-Gal4>LKB1-GFP larval NMJs are shown.

FIG. 21 shows localization of LKB1-GFP at the larval NMJ. Double-labeling with anti-HRP and anti-GFP of wild-type, elav-Gal4>LKB1-GFP, or Mhc-Gal4>LKB1-GFP larval NMJs are shown. Scale bars: 5 µm.

Figure 22:
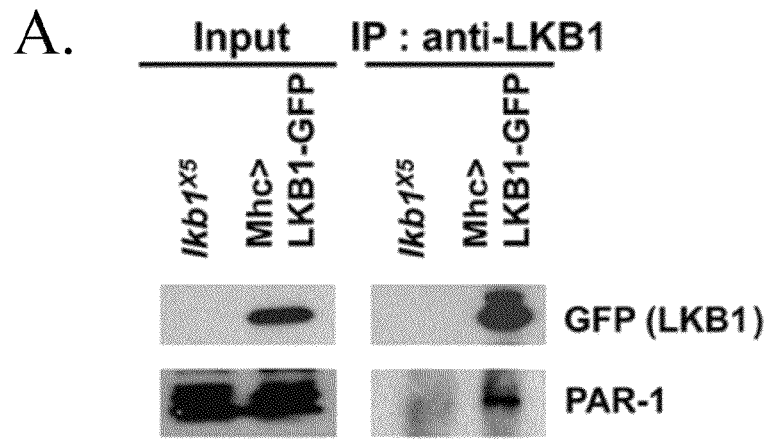
FIGS. 22A-C show in vivo physical interaction between LKB1 and PAR-1 and effects of LKB1 GOF on synaptic morphology.
Figure 22:
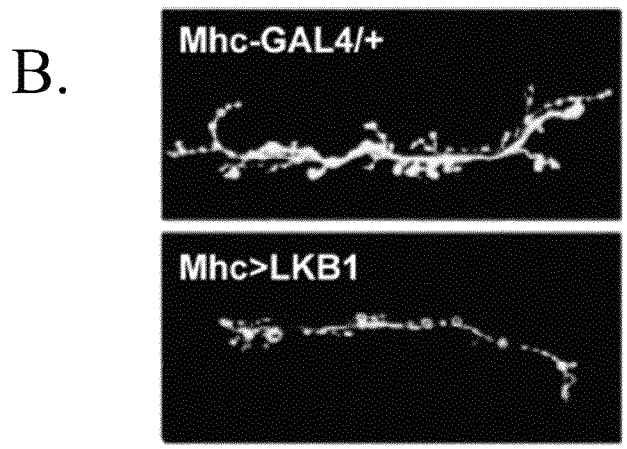
Figure 22:
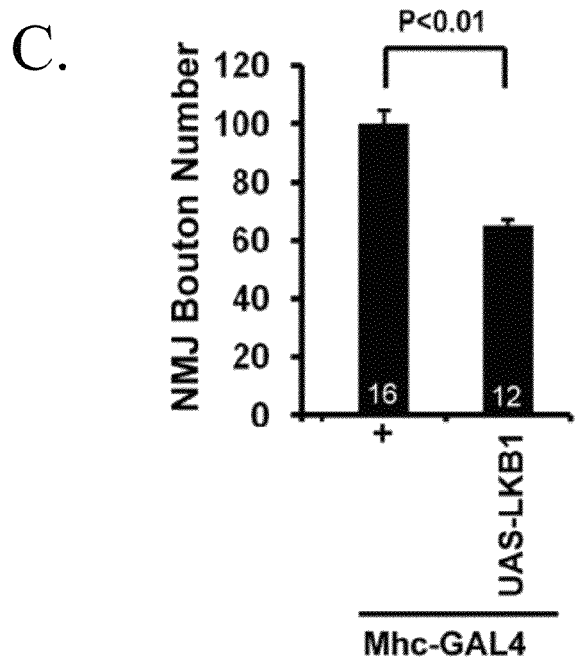

FIG. 22 shows in vivo physical interaction between LKB1 and PAR-1 and effects of LKB1 GOF on synaptic morphology. (a) PAR-1 physically interacts with LKB1. Larval body-wall muscle extracts from Mhc-Gal4>UAS-LKB1-GFP or lkb1$^{X5}$ null mutant animals were immunoprecipitated with anti-LKB1, and the presence of endogenous PAR-1 in the IP complex was detected by western blot analysis with an anti-PAR-1 antibody. (b) Representative immunostaining showing larval NMJ morphology in animals overexpressing LKB1 pre- or post-synaptically. (c) Quantification of data shown in B. The total number of boutons per muscle area on muscle 6/7 of A3 is measured. N indicates the number of animals analyzed. The error bars represent means±SEM. P-values were determined using two-tailed Student's t-test for each comparison. Experiments were performed in triplicate.

FIG. 23 shows postsynaptic overexpression of APP or Aβ42 leads to a decrease in NMJ bouton number. Representative HRP immunostainings showing larval NMJ morphology of the indicated genotypes are shown. Mhc-Gal4/+ and Mhc-Gal4>UAS-APP were grown at 29° C. and Mhc-Gal4>UAS-Aβ42 at 25° C. Scale bar, 50 µm.

Figure 24:
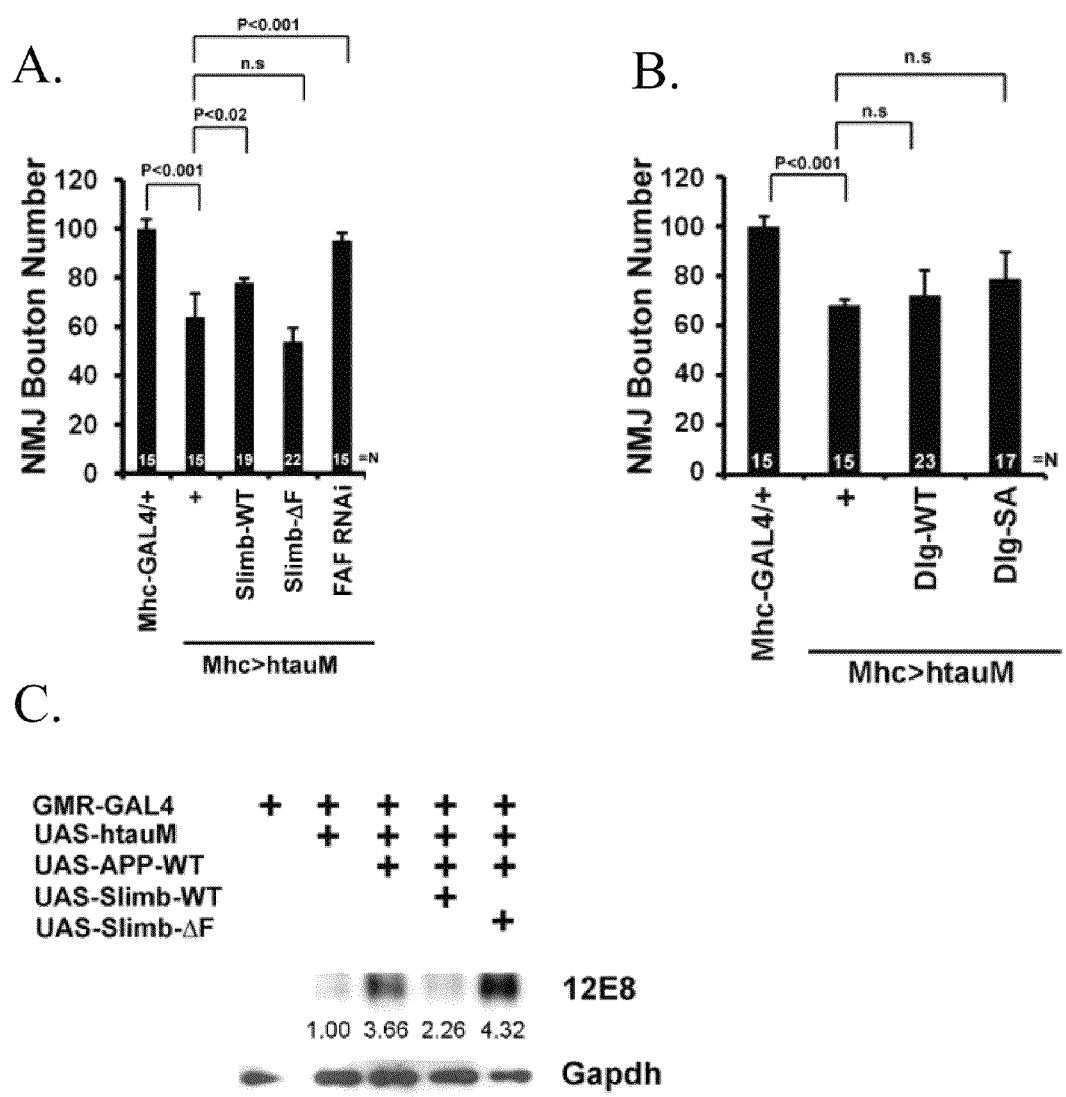
FIGS. 24A-C shows genetic interactions between tau and Slimb/FAF or between tau and Dlg, and the effects of APP and Slimb interaction on tau phosphorylation at 12E8 sites.

FIG. 24 shows genetic interactions between tau and Slimb/FAF or between tau and Dlg, and the effects of APP and Slimb interaction on tau phosphorylation at 12E8 sites. (a) Quantification of larval NMJ bouton number showing genetic interaction between htauM and Slimb or FAF. The synapse loss phenotype seen in Mhc-Gal4>UAS-htauM background was partially rescued by the co-expression of Slimb-WT or FAF RNAi. N indicates the number of animals analyzed. The error bars represent means±SEM. P-values were determined using two-tailed Student's t-test for each comparison. Experiments were performed in triplicate. (b) Quantification of NMJ bouton number testing possible genetic interaction between htauM and Dlg variants at the NMJ. N indicates the number of animals analyzed. No interaction was detected. N indicates the number of animals analyzed. The error bars represent means±SEM. P-values were determined using two-tailed Student's t-test for each comparison. Experiments were performed in triplicate. (c) Western blot analysis of 12E8-positive p-htau level after co-expression of Slimb-WT or Slimb-ΔF in GMR-Gal4>UAS-htauM+UAS-APP-WT background. Gapdh serves as a loading control. Values represent 12E8-positive p-tau level in the indicated genotypes normalized with GMR-Gal4>UAS-htauM control in three independent experiments. Experiments were performed in triplicate.

Figure 25:
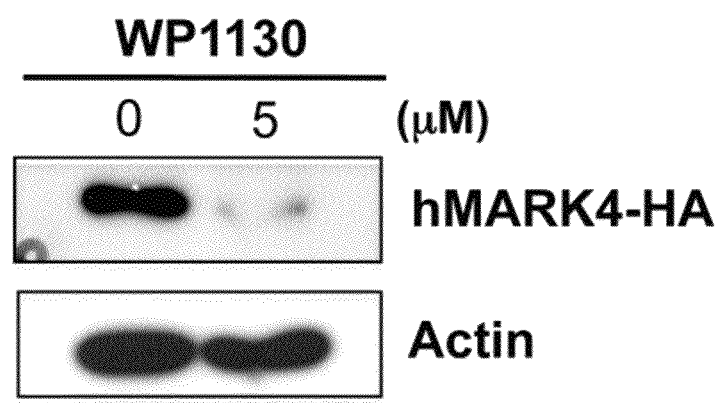
FIG. 25A-B show that WP1130 effectively blocked PAR-1 toxicity in mammalian cells.
Figure 25:
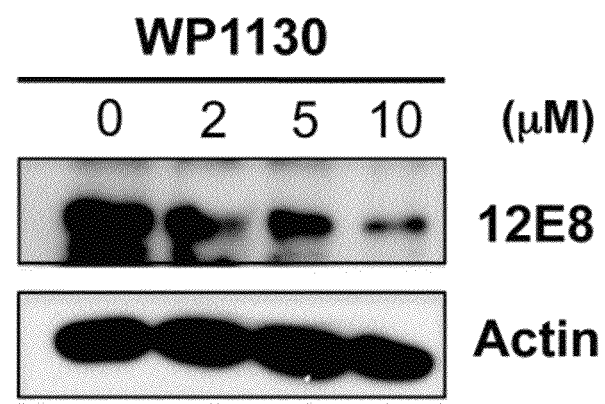

FIG. 25 shows that WP1130 effectively blocked PAR-1 toxicity in mammalian cells. (a) WP1130 treatment decreases the stability of MARK4. HEK 293T cells transfected with the hMARK4-HA plasmids were treated with 5 µM WP1130 for 8 h and subsequently used for western blot analysis. Actin serves as loading control. (b) WP1130 treatment decreased endogenous tau phosphorylation at the MARK sites (recognized by 12E8 antibody). Cultured HEK 293T cells were treated with 0, 2, 5 and 10 µM WP1130 for 12 h, and used for western blot analysis. Actin serves as loading control.

FIG. 26 shows pharmacological rescue of postsynaptic toxicity of PAR-1 by small-molecule WP1130. (a) Quantification of the pharmacological effect of WP1130 on the total number of boutons on muscle 6/7 of A3, after normalization with bouton area. Indicated genotype flies were incubated with 0, 2, 5 or 10 µM concentrations of WP1130. (b) Western blot analyses showing the effects of WP1130 (10 µM) on PAR-1-Myc levels in third instar larvae body-wall muscle extracts. Values represent normalized PAR-1-Myc levels. Actin serves as loading control. (c) Quantification of NMJ bouton number showing rescue by WP1130 (10 µM) of the bouton-loss phenotypes induced by Mhc-Gal4>UAS-htauM or Mhc-Gal4>UAS-htauM+UAS-PAR-1. (d) Western blot analysis showing reduced 12E8-positive htauM level by WP1130 (10 µM). Values represent normalized 12E8-positive htauM levels. Actin serves as loading control. (e) Quantification of NMJ bouton number showing rescue by WP1130 (10 µM) of the bouton-loss phenotypes induced the expression APP/Aβ-42. (f) A model depicting possible signaling pathways linking APP/Aβ-42 to synaptic dysfunction and synapse loss seen in AD. Dashed lines indicate potential direct regulations.

FIG. 27 shows western blot analysis of the effects of WP1130 treatment on MARK4 protein stability and on tau phosphorylation at the PAR-1/MARK target site (S262). Tauopathy mice (PS19) expressing the pathogenic P301S human tau transgene were treated with vehicle (#1, 2, 4, 6, 12) or WP1130 (#5, 8, 13, 14, 15) by intracerebroventricular (ICV) infusion, and brain extracts were subjected to Western blot analysis with the indicated antibodies. Actin serves as a loading control, and T14 anti-Tau antibody measures levels of total tau. Note the reduction of MARK4 and p-Tau (S262) protein levels by drug treatment.

FIG. 28 shows results of a behavioral assay showing rescue of cognitive deficit of PS19 mice by WP1130 treatment. (Top) A diagram showing the passive-avoidance test, in which animals were allow to freely moving between the light and dark chambers during habituation. During training, the animals were subjected to electric shock on the foot in the dark chamber. During testing, the trained animals were placed in the light chamber and the time it took the animals to enter the dark chamber (latency time) was recorded. (Bottom) Statistical analysis of the latency times of vehicle-treated WT control, vehicle-treated PS19 tauopathy mice, and drug-treated PS19 tauopathy during the habituation, training, and testing periods. ** indicates P<0.01 in Student's t-test.

REFERENCES

1 Guo, S. & Kemphues, K. J. par-1, a gene required for establishing polarity in *C. elegans* embryos, encodes a putative Ser/Thr kinase that is asymmetrically distributed. *Cell* 81, 611-620 (1995).

2 Matenia, D. & Mandelkow, E. M. The tau of MARK: a polarized view of the cytoskeleton. *Trends Biochem Sci* 34, 332-342 (2009).

3 Hurov, J. & Piwnica-Worms, H. The Par-1/MARK family of protein kinases: from polarity to metabolism. *Cell Cycle* 6, 1966-1969 (2007).

4 Drewes, G., Ebneth, A., Preuss, U., Mandelkow, E. M. & Mandelkow, E. MARK, a novel family of protein kinases that phosphorylate microtubule-associated proteins and trigger microtubule disruption. *Cell* 89, 297-308 (1997).

5 Trinczek, B., Brajenovic, M., Ebneth, A. & Drewes, G. MARK4 is a novel microtubule-associated proteins/microtubule affinity-regulating kinase that binds to the cellular microtubule network and to centrosomes. *J Biol Chem* 279, 5915-5923 (2004).

6 Nishimura, I., Yang, Y. & Lu, B. PAR-1 kinase plays an initiator role in a temporally ordered phosphorylation process that confers tau toxicity in *Drosophila*. *Cell* 116, 671-682 (2004).

7 Lee, V. M., Goedert, M. & Trojanowski, J. Q. Neurodegenerative tauopathies. *Annu Rev Neurosci* 24, 1121-1159 (2001).

8 Timm, T. et al. MARKK, a Ste20-like kinase, activates the polarity-inducing kinase MARK/PAR-1. *EMBO J* 22, 5090-5101 (2003).

9 Lizcano, J. M. et al. LKB1 is a master kinase that activates 13 kinases of the AMPK subfamily, including MARK/PAR-1. *EMBO J* 23, 833-843 (2004).

10 Wang, J. W., Imai, Y. & Lu, B. Activation of PAR-1 kinase and stimulation of tau phosphorylation by diverse signals require the tumor suppressor protein LKB1. *J Neurosci* 27, 574-581 (2007).

11 Hershko, A. & Ciechanover, A. The ubiquitin system. *Annu Rev Biochem* 67, 425-479 (1998).

12 Schwartz, A. L. & Ciechanover, A. Targeting proteins for destruction by the ubiquitin system: implications for human pathobiology. *Annu Rev Pharmacol Toxicol* 49, 73-96 (2009).

13 Jiang, J. Regulation of Hh/Gli signaling by dual ubiquitin pathways. *Cell Cycle* 5, 2457-2463 (2006).

14 Jiang, J. & Struhl, G. Regulation of the Hedgehog and Wingless signalling pathways by the F-box/WD40-repeat protein Slimb. *Nature* 391, 493-496 (1998).

15 Winston, J. T. et al. The SCFbeta-TRCP-ubiquitin ligase complex associates specifically with phosphorylated destruction motifs in IkappaBalpha and beta-catenin and stimulates IkappaBalpha ubiquitination in vitro. *Genes Dev* 13, 270-283 (1999).

16 Ho, M. S., Ou, C., Chan, Y. R., Chien, C. T. & Pi, H. The utility F-box for protein destruction. *Cell Mol Life Sci* 65, 1977-2000 (2008).

17 Nijman, S. M. et al. A genomic and functional inventory of deubiquitinating enzymes. *Cell* 123, 773-786 (2005).

18 DiAntonio, A. et al. Ubiquitination-dependent mechanisms regulate synaptic growth and function. *Nature* 412, 449-452 (2001).

19 Holtzman, D. M., Morris, J. C. & Goate, A. M. Alzheimer's disease: the challenge of the second century. *Sci Transl Med* 3, 77sr71 (2011).

20 Xue, L. et al. Tumor suppressor CYLD regulates JNK-induced cell death in *Drosophila. Dev Cell* 13, 446-454 (2007).

21 Zhang, Y. et al. PAR-1 kinase phosphorylates Dlg and regulates its postsynaptic targeting at the *Drosophila* neuromuscular junction. *Neuron* 53, 201-215 (2007).

22 Brajenovic, M., Joberty, G., Kuster, B., Bouwmeester, T. & Drewes, G. Comprehensive proteomic analysis of human Par protein complexes reveals an interconnected protein network. *J Biol Chem* 279, 12804-12811 (2004).

23 Al-Hakim, A. K. et al. Control of AMPK-related kinases by USP9X and atypical Lys(29)/Lys(33)-linked polyubiquitin chains. *Biochem J* 411, 249-260 (2008).

24 Chen, X., Zhang, B. & Fischer, J. A. A specific protein substrate for a deubiquitinating enzyme: Liquid facets is the substrate of Fat facets. *Genes Dev* 16, 289-294 (2002).

25 Mortimer, N. T. & Moberg, K. H. The *Drosophila* F-box protein Archipelago controls levels of the Trachealess transcription factor in the embryonic tracheal system. *Dev Biol* 312, 560-571 (2007).

26 Iijima, K., Gatt, A. & Iijima-Ando, K. Tau Ser262 phosphorylation is critical for Abeta42-induced tau toxicity in a transgenic *Drosophila* model of Alzheimer's disease. *Hum Mol Genet* 19, 2947-2957 (2010).

27 Haass, C. & Selkoe, D. J. Soluble protein oligomers in neurodegeneration: lessons from the Alzheimer's amyloid beta-peptide. *Nat Rev Mol Cell Biol* 8, 101-112 (2007).

28 Ittner, L. M. & Gotz, J. Amyloid-beta and tau-a toxic pas de deux in Alzheimer's disease. *Nat Rev Neurosci* 12, 65-72 (2011).

29 Ittner, L. M. et al. Dendritic function of tau mediates amyloid-beta toxicity in Alzheimer's disease mouse models. *Cell* 142, 387-397 (2010).

30 Hoover, B. R. et al. Tau mislocalization to dendritic spines mediates synaptic dysfunction independently of neurodegeneration. *Neuron* 68, 1067-1081 (2010).

31 Heidary, G. & Fortini, M. E. Identification and characterization of the *Drosophila* tau homolog. *Mech Dev* 108, 171-178 (2001).

32 Lee, S., Liu, H. P., Lin, W. Y., Guo, H. & Lu, B. LRRK2 kinase regulates synaptic morphology through distinct substrates at the presynaptic and postsynaptic compartments of the *Drosophila* neuromuscular junction. *J Neurosci* 30, 16959-16969 (2010).

33 DiAntonio, A. & Hicke, L. Ubiquitin-dependent regulation of the synapse. *Annu Rev Neurosci* 27, 223-246 (2004).

34 Yi, J. J. & Ehlers, M. D. Emerging roles for ubiquitin and protein degradation in neuronal function. *Pharmacol Rev* 59, 14-39 (2007).

35 Selkoe, D. J. Alzheimer's disease is a synaptic failure. *Science* 298, 789-791 (2002).

36 Xu, J., Taya, S., Kaibuchi, K. & Arnold, A. P. Spatially and temporally specific expression in mouse hippocampus of Usp9x, a ubiquitin-specific protease involved in synaptic development. *J Neurosci Res* 80, 47-55 (2005).

37 Xu, J. Age-related changes in Usp9x protein expression and DNA methylation in mouse brain. *Brain Res Mol Brain Res* 140, 17-24 (2005).

38 Chin, J. Y. et al. Microtubule-affinity regulating kinase (MARK) is tightly associated with neurofibrillary tangles in Alzheimer brain: a fluorescence resonance energy transfer study. *J Neuropathol Exp Neurol* 59, 966-971 (2000).

39 Augustinack, J. C., Schneider, A., Mandelkow, E. M. & Hyman, B. T. Specific tau phosphorylation sites correlate with severity of neuronal cytopathology in Alzheimer's disease. *Acta Neuropathol (Berl)* 103, 26-35 (2002).

40 Perez, M. et al. Characterization of a double (amyloid precursor protein-tau) transgenic: tau phosphorylation and aggregation. *Neuroscience* 130, 339-347 (2005).

41 Zempel, H., Thies, E., Mandelkow, E. & Mandelkow, E. M. Abeta oligomers cause localized Ca(2+) elevation, missorting of endogenous Tau into dendrites, Tau phosphorylation, and destruction of microtubules and spines. *J Neurosci* 30, 11938-11950 (2010).

42 Gylys, K. H. et al. Synaptic changes in Alzheimer's disease: increased amyloid-beta and gliosis in surviving terminals is accompanied by decreased PSD-95 fluorescence. *Am J Pathol* 165, 1809-1817 (2004).

43 Almeida, C. G. et al. Beta-amyloid accumulation in APP mutant neurons reduces PSD-95 and GluR1 in synapses. *Neurobiol Dis* 20, 187-198 (2005).

44 Seshadri, S. et al. Genome-wide analysis of genetic loci associated with Alzheimer disease. *JAMA* 303, 1832-1840 (2010).

45 Kim, E. & Sheng, M. PDZ domain proteins of synapses. *Nat Rev Neurosci* 5, 771-781 (2004).

46 Yu, W. et al. A critical role for the PAR-1/MARK-tau axis in mediating the toxic effects of Abeta on synapses and dendritic spines. *Hum Mol Genet* 21, 1384-1390 (2011).

47 Lee, F. K. et al. The role of ubiquitin linkages on alpha-synuclein induced-toxicity in a *Drosophila* model of Parkinson's disease. *J Neurochem* 110, 208-219 (2009).

48 Grima, B. et al. The F-box protein slimb controls the levels of clock proteins period and timeless. *Nature* 420, 178-182 (2002).

49 Martin, S. G. & St Johnston, D. A role for *Drosophila* LKB1 in anterior-posterior axis formation and epithelial polarity. *Nature* 421, 379-384 (2003).

50 Ko, H. W., Jiang, J. & Edery, I. Role for Slimb in the degradation of *Drosophila* Period protein phosphorylated by Doubletime. *Nature* 420, 673-678 (2002).

51 Lee, S., Liu, H. P., Lin, W. Y., Guo, H. & Lu, B. LRRK2 kinase regulates synaptic morphology through distinct substrates at the presynaptic and postsynaptic compartments of the *Drosophila* neuromuscular junction. *J Neurosci* 30, 16959-16969 (2010).

52 Bartholomeusz G A et al. Blood. 109:3470-8, (2007) Activation of a novel Bcr/Abl destruction pathway by WP1130 induces apoptosis of chronic myelogenous leukemia cells.

53 Kapuria V et al. Cancer Res. 70:9265-76, (2010) Deubiquitinase Inhibition by Small-Molecule WP1130 Triggers Aggresome Formation and Tumor Cell Apoptosis.

What is claimed is:

1. A composition for treating Alzheimer's disease, the composition comprising a USP-9x inhibitor having the structure:

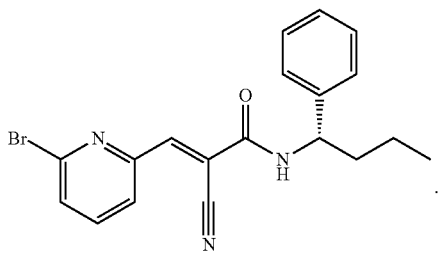 [SMILES: CCC[C@H](NC(=O)/C(C#N)=C/c1cccc(Br)n1)c1ccccc1]

2. The composition of claim 1, further comprising a pharmaceutically acceptable carrier.

3. The composition of claim 1, wherein the USP-9x inhibitor is present in a therapeutically effective amount.

4. The composition of claim 1, wherein the USP-9x inhibitor is present in a prophylactically effective amount.

5. The composition of claim 1, wherein the SCF(β-TrCP) enhancer is present in a therapeutically effective amount.

6. The composition of claim 1, wherein the SCF(β-TrCP) enhancer is present in a prophylactically effective amount.

7. The composition of claim 1, wherein the SCF(β-TrCP) enhancer is a gene therapy.

8. The composition of claim 1, wherein the SCF(β-TrCP) enhancer increases the neddylation of Cullin.

9. The composition of claim 8, wherein the SCF(β-TrCP) enhancer increases the expression or activity of NEDD8 or NAE.

10. The composition of claim 8, wherein the SCFM(β-TrCP) enhancer is a gene therapy that increases expression of NEDD8 or NAE.

11. The composition of claim 8, wherein the SCFM(β-TrCP) enhancer is a small molecule activator of NAE.

12. The composition of claim 8, wherein the SCFM(β-TrCP) enhancer increases activity and/or expression of CAND1.

13. The composition of claim 8, wherein the SCFM(β-TrCP) enhancer increases expression of CAND1 by a gene therapy.

14. The composition of claim 8, wherein the SCFM(β-TrCP) enhancer increases activity of CAND1 through administration of a small molecule activator of CAND1.

15. The composition of claim 8, wherein the SCFM(β-TrCP) enhancer decreases Cullin deneddylation.

16. The composition of claim 15, wherein the SCFM(β-TrCP) enhancer inhibits CSN.

17. The composition of claim 15, wherein the SCFM(β-TrCP) enhancer is RNAi targeting CSN.

18. The composition of claim 17, wherein the RNAi is miRNA targeting CSN.

19. The composition of claim 17, wherein the RNAi is sRNA targeting CSN.

20. The composition of claim 17, wherein, the RNAi is shRNA targeting CSN.

21. The composition of claim 17, wherein the SCFM(β-TrCP) enhancer is a small molecule inhibitor of CSN.

22. A kit comprising a USP-9x inhibitor having the structure:

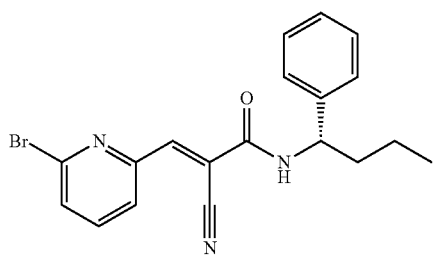 [SMILES: CCC[C@H](NC(=O)/C(C#N)=C/c1cccc(Br)n1)c1ccccc1]

a SCFM(β-TrCP) enhancer; and a pharmaceutically acceptable carrier thereof.

23. The kit of claim 22, wherein the inhibitor and the enhancer are coformulated.

24. The kit of claim 22, wherein the inhibitor and the enhancer are copackaged.

25. The kit of claim 22, further comprising instructions for treatment of Alzheimer's disease.

26. The composition of claim 1, wherein the composition is effective in treating tauopathies selected from the group consisting of: Creutzfeldt-Jakob disease, dementia pugilistica, Down's syndrome, Gerstmann-Straussler-Sheinker disease, inclusion-body myositis, frontotemporal dementia (FTD), Pick's disease, tangle-predominant Alzheimer's disease, corticobasal degeneration, amyotrophic lateral sclerosis/parkinsonism-dementia complex, argyrophilic grain dementia, diffuse neurofibrillary tangles with calcification, Hallevorden-Spatz disease, multiple system atrophy, Niemann-Pick disease, Type C1 progressive subcortial gliosis, progressive supranuclear palsy and subacute sclerosing panencephalitis.

\* \* \* \* \*